US012788274B2

(12) United States Patent
Ransbury et al.

(10) Patent No.: US 12,788,274 B2
(45) Date of Patent: Nov. 10, 2026

(54) SYSTEMS AND METHODS FOR OPTIMIZING TISSUE ABLATION

(71) Applicant: 460MEDICAL, INC., Weston, MA (US)

(72) Inventors: Terrance J. Ransbury, Chapel Hill, NC (US); Omar Amirana, Weston, MA (US)

(73) Assignee: 460MEDICAL, INC., Weston, MA (US)

(*) Notice: Subject to any disclaimer, the term of this patent is extended or adjusted under 35 U.S.C. 154(b) by 1247 days.

(21) Appl. No.: 17/453,738

(22) Filed: Nov. 5, 2021

(65) Prior Publication Data

US 2022/0133172 A1 May 5, 2022

Related U.S. Application Data

(60) Provisional application No. 63/110,135, filed on Nov. 5, 2020.

(51) Int. Cl.
*A61B 5/107* (2006.01)
*A61B 5/00* (2006.01)

(52) U.S. Cl.
CPC .......... *A61B 5/1076* (2013.01); *A61B 5/0084* (2013.01)

(58) Field of Classification Search
None
See application file for complete search history.

(56) References Cited

U.S. PATENT DOCUMENTS 3,387,305 A 6/1968 Shafer
3,831,467 A 8/1974 Moore
(Continued)

FOREIGN PATENT DOCUMENTS

CN 1289239 3/2001
CN 1764419 4/2006
(Continued)

OTHER PUBLICATIONS

International Search Report based on PCT/US2021/058262 dated Jan. 31, 2022.
(Continued)

*Primary Examiner* — Charles A Marmor, II
*Assistant Examiner* — Marc D. Honrath
(74) *Attorney, Agent, or Firm* — Greenberg Traurig, LLP; David J. Dykeman; Roman Fayerberg

(57) ABSTRACT

Systems and methods for ablation optimization are provided. In some embodiments, a catheter system is provided for determining tissue thickness and includes a catheter including a catheter body with a distal tip, source openings in the distal tip for passing light energy to tissue, and detector openings in the distal tip for passing light energy from tissue. A visualization system includes a light source, a light measuring instrument, and optical fibers extending through the catheter body. The optical fibers include source fibers to pass light energy to the tissue through the source openings and detector fibers to detect light energy from the tissue through the detector openings. The source and detector openings are aligned in a longitudinal arrangement along a length of the distal tip and are paired and spaced apart from one another by a separation distance calculated based on a thickness of the tissue to be measured.

26 Claims, 11 Drawing Sheets

(56) References Cited

U.S. PATENT DOCUMENTS 4,024,873 A 5/1977 Antoshkiw et al.
4,619,247 A 10/1986 Inoue et al.
5,074,306 A 12/1991 Green et al.
5,187,572 A 2/1993 Nakamura et al.
5,350,375 A 9/1994 Deckelbaum et al.
5,419,323 A 5/1995 Kittrell et al.
5,421,337 A 6/1995 Richards-Kortum et al.
5,507,287 A 4/1996 Palcic et al.
5,540,681 A 7/1996 Strul et al.
5,584,799 A 12/1996 Gray
5,590,660 A 1/1997 MacAulay et al.
5,657,760 A 8/1997 Ying et al.
5,713,364 A 2/1998 DeBaryshe et al.
5,749,830 A 5/1998 Kaneko et al.
5,833,688 A 11/1998 Sieben et al.
5,885,258 A 3/1999 Sachdeva et al.
5,904,651 A 5/1999 Swanson et al.
5,954,665 A 9/1999 Ben Haim
6,064,069 A 5/2000 Nakano et al.
6,112,123 A 8/2000 Kelleher et al.
6,124,597 A 9/2000 Shehada et al.
6,174,291 B1 1/2001 McMahon et al.
6,178,346 B1 1/2001 Amundson et al.
6,197,021 B1 3/2001 Panescu et al.
6,208,886 B1 3/2001 Alfano et al.
6,217,573 B1 4/2001 Webster et al.
6,219,566 B1 4/2001 Weersink et al.
6,251,107 B1 6/2001 Schaer
6,289,236 B1 9/2001 Koenig et al.
6,309,352 B1 10/2001 Oraevsky et al.
6,343,228 B1 1/2002 Qu
6,423,055 B1 7/2002 Farr et al.
6,423,057 B1 7/2002 He et al.
6,450,971 B1 9/2002 Andrus et al.
6,485,413 B1 11/2002 Boppart et al.
6,516,217 B1 2/2003 Tsujita
6,522,913 B2 2/2003 Swanson et al.
6,542,767 B1 4/2003 McNichols et al.
6,572,609 B1 6/2003 Farr et al.
6,584,360 B2 6/2003 Francischelli et al.
6,626,900 B1 9/2003 Sinofsky et al.
6,648,883 B2 11/2003 Francischelli et al.
6,658,279 B2 12/2003 Swanson et al.
6,663,622 B1 12/2003 Foley et al.
6,663,627 B2 12/2003 Francischelli et al.
6,671,535 B1 12/2003 McNichols et al.
6,697,657 B1 2/2004 Shehada et al.
6,706,038 B2 3/2004 Francischelli et al.
6,716,196 B2 4/2004 Lesh et al.
6,743,225 B2 6/2004 Sanchez et al.
6,746,401 B2 6/2004 Panescu
6,761,716 B2 7/2004 Kadhiresan et al.
6,825,928 B2 11/2004 Liu et al.
6,936,047 B2 8/2005 Nasab et al.
6,937,885 B1 8/2005 Lewis et al.
6,942,657 B2 9/2005 Sinofsky et al.
6,953,457 B2 10/2005 Farr et al.
6,974,454 B2 12/2005 Hooven
6,975,898 B2 12/2005 Seibel
6,975,899 B2 12/2005 Faupel et al.
6,979,290 B2 12/2005 Mourlas et al.
6,989,010 B2 1/2006 Francischelli et al.
7,001,383 B2 2/2006 Keidar
7,029,470 B2 4/2006 Francischelli et al.
7,047,068 B2 5/2006 Haissaguerre
7,130,672 B2 10/2006 Pewzner et al.
7,192,427 B2 3/2007 Chapelon et al.
7,207,984 B2 4/2007 Farr et al.
7,232,437 B2 6/2007 Berman et al.
7,235,045 B2 6/2007 Wang et al.
7,250,048 B2 7/2007 Francischelli et al.
7,252,664 B2 8/2007 Nasab et al.
7,255,695 B2 8/2007 Falwell et al.
7,289,205 B2 10/2007 Yaroslavsky et al.
7,306,593 B2 12/2007 Keidar et al.
7,338,485 B2 3/2008 Brucker et al.
7,357,796 B2 4/2008 Farr et al.
7,367,944 B2 5/2008 Rosemberg et al.
7,367,972 B2 5/2008 Francischelli et al.
7,417,740 B2 8/2008 Alphonse et al.
7,497,858 B2 3/2009 Chapelon et al.
7,527,625 B2 5/2009 Knight et al.
7,534,204 B2 5/2009 Starksen et al.
7,539,530 B2 5/2009 Caplan et al.
7,587,236 B2 9/2009 Demos et al.
7,591,816 B2 9/2009 Wang et al.
7,596,404 B2 9/2009 Maier et al.
7,598,088 B2 10/2009 Balas
7,640,046 B2 12/2009 Pastore
7,662,152 B2 2/2010 Sharareh et al.
7,681,579 B2 3/2010 Schwartz
7,727,229 B2 6/2010 He et al.
7,727,231 B2 6/2010 Swanson
7,729,750 B2 6/2010 Tromberg et al.
7,766,907 B2 8/2010 Dando et al.
7,776,033 B2 8/2010 Swanson
7,822,460 B2 10/2010 Halperin et al.
7,824,397 B2 11/2010 McAuley
7,824,399 B2 11/2010 Francischelli et al.
7,837,676 B2 11/2010 Sinelnikov et al.
7,846,157 B2 12/2010 Kozel
7,862,561 B2 1/2011 Swanson et al.
7,877,128 B2 1/2011 Schwartz
7,918,850 B2 4/2011 Govari et al.
7,930,016 B1 4/2011 Saadat
7,942,871 B2 5/2011 Thapliyal et al.
7,950,397 B2 5/2011 Thapliyal et al.
7,974,683 B2 7/2011 Balas et al.
7,976,537 B2 7/2011 Lieber et al.
7,979,107 B2 7/2011 Lin et al.
7,992,573 B2 8/2011 Wilson et al.
7,996,078 B2 8/2011 Paul et al.
8,007,433 B2 8/2011 Iketani
8,024,027 B2 9/2011 Freeman et al.
8,025,661 B2 9/2011 Arnold et al.
8,050,746 B2 11/2011 Saadat et al.
8,078,266 B2 12/2011 Saadat et al.
8,123,742 B2 2/2012 Berger
8,123,745 B2 2/2012 Beeckler et al.
8,129,105 B2 3/2012 Zuckerman
8,131,350 B2 3/2012 Saadat et al.
8,137,333 B2 3/2012 Saadat et al.
8,144,966 B2 3/2012 Provenzano et al.
8,146,603 B2 4/2012 Thapliyal et al.
8,147,484 B2 4/2012 Lieber et al.
8,152,795 B2 4/2012 Farr et al.
8,160,680 B2 4/2012 Boyden et al.
8,175,688 B2 5/2012 Lewis et al.
8,180,436 B2 5/2012 Boyden et al.
8,188,446 B2 5/2012 Ohno
8,195,271 B2 6/2012 Rahn
8,203,709 B2 6/2012 Ishii
8,219,183 B2 7/2012 Mashke et al.
8,221,310 B2 7/2012 Saadat et al.
8,235,985 B2 8/2012 Saadat et al.
8,241,272 B2 8/2012 Arnold et al.
8,267,926 B2 9/2012 Paul et al.
8,277,444 B2 10/2012 Arnold et al.
8,298,227 B2 10/2012 Leo et al.
8,309,346 B2 11/2012 Zuckerman
8,317,783 B2 11/2012 Cao et al.
8,333,012 B2 12/2012 Rothe et al.
8,353,907 B2 1/2013 Winkler et al.
8,357,149 B2 1/2013 Govari et al.
8,366,705 B2 2/2013 Arnold et al.
8,369,922 B2 2/2013 Paul et al.
8,374,682 B2 2/2013 Freeman et al.
8,382,750 B2 2/2013 Brannan
8,403,925 B2 3/2013 Miller et al.
8,414,508 B2 4/2013 Thapliyal et al.
8,417,321 B2 4/2013 Saadat et al.
8,417,323 B2 4/2013 Uzunbajakava et al.
8,419,613 B2 4/2013 Saadat et al.
8,435,232 B2 5/2013 Aeby et al.

(56) References Cited

U.S. PATENT DOCUMENTS

| | | | |
|---|---|---|---|
| 8,444,639 | B2 | 5/2013 | Arnold et al. |
| 8,460,285 | B2 | 6/2013 | Wang et al. |
| 8,463,366 | B2 | 6/2013 | Freeman et al. |
| 8,500,730 | B2 | 8/2013 | Lee et al. |
| 8,504,132 | B2 | 8/2013 | Friedman et al. |
| 8,511,317 | B2 | 8/2013 | Thapliyal et al. |
| 8,540,704 | B2 | 9/2013 | Melsky et al. |
| 8,548,567 | B2 | 10/2013 | Maschke et al. |
| 8,556,892 | B2 | 10/2013 | Hong et al. |
| 8,583,220 | B2 | 11/2013 | Schwartz |
| 8,603,084 | B2 | 12/2013 | Fish et al. |
| 8,607,800 | B2 | 12/2013 | Thapliyal et al. |
| 8,628,520 | B2 | 1/2014 | Sharareh et al. |
| 8,641,705 | B2 | 2/2014 | Leo et al. |
| 8,641,706 | B2 | 2/2014 | Lieber et al. |
| 8,690,758 | B2 | 4/2014 | Matsumoto |
| 8,702,690 | B2 | 4/2014 | Paul et al. |
| 8,709,008 | B2 | 4/2014 | Willis et al. |
| 8,728,077 | B2 | 5/2014 | Paul et al. |
| 8,755,860 | B2 | 6/2014 | Paul et al. |
| 8,774,906 | B2 | 7/2014 | Harks et al. |
| 8,808,281 | B2 | 8/2014 | Emmons et al. |
| 8,849,380 | B2 | 9/2014 | Patwardhan |
| 8,858,495 | B2 | 10/2014 | Tegg et al. |
| 8,876,817 | B2 | 11/2014 | Avitall et al. |
| 8,882,697 | B2 | 11/2014 | Celermajer et al. |
| 8,894,589 | B2 | 11/2014 | Leo et al. |
| 8,894,641 | B2 | 11/2014 | Brannan |
| 8,900,219 | B2 | 12/2014 | Sinofsky et al. |
| 8,900,225 | B2 | 12/2014 | Bar-Tal et al. |
| 8,900,228 | B2 | 12/2014 | Grunewald et al. |
| 8,900,229 | B2 | 12/2014 | Govari et al. |
| 8,906,011 | B2 | 12/2014 | Gelbart et al. |
| 8,915,878 | B2 | 12/2014 | Winkler et al. |
| 8,923,959 | B2 | 12/2014 | Boveja et al. |
| 8,926,604 | B2 | 1/2015 | Govari et al. |
| 8,929,973 | B1 | 1/2015 | Webb et al. |
| 8,948,851 | B2 | 2/2015 | Leblond et al. |
| 8,951,247 | B2 | 2/2015 | Ding et al. |
| 8,986,292 | B2 | 3/2015 | Sliwa et al. |
| 8,986,298 | B2 | 3/2015 | Lee et al. |
| 8,998,890 | B2 | 4/2015 | Paul et al. |
| 8,998,892 | B2 | 4/2015 | Winkler et al. |
| 8,998,893 | B2 | 4/2015 | Avitall |
| 9,008,746 | B2 | 4/2015 | Pastore et al. |
| 9,014,789 | B2 | 4/2015 | Mercader et al. |
| 9,084,611 | B2 | 7/2015 | Amirana et al. |
| 9,087,368 | B2 | 7/2015 | Tearney et al. |
| 9,186,066 | B2 | 11/2015 | Tearney et al. |
| 9,220,411 | B2 | 12/2015 | Hillman |
| 9,233,241 | B2 | 1/2016 | Long |
| 9,277,865 | B2 | 3/2016 | Yamaguchi et al. |
| 10,076,238 | B2 | 9/2018 | Amirana et al. |
| 10,143,517 | B2 | 12/2018 | Ransbury et al. |
| 10,568,535 | B2 | 2/2020 | Roberts et al. |
| 10,682,179 | B2 | 6/2020 | Ransbury et al. |
| 10,716,462 | B2 | 7/2020 | Amirana et al. |
| 10,722,301 | B2 | 7/2020 | Amirana et al. |
| 10,736,512 | B2 | 8/2020 | Mercader et al. |
| 10,779,904 | B2 | 9/2020 | Ransbury et al. |
| 11,096,584 | B2 | 8/2021 | Mercader et al. |
| 11,457,817 | B2 | 10/2022 | Sarvazyan |
| 11,559,192 | B2 | 1/2023 | Amirana et al. |
| 11,559,352 | B2 | 1/2023 | Amirana et al. |
| 12,075,980 | B2 | 9/2024 | Amirana et al. |
| 12,076,081 | B2 | 9/2024 | Amirana et al. |
| 12,539,043 | B2 | 2/2026 | Sarvazyan |
| 2002/0042556 | A1 | 4/2002 | Sugimoto et al. |
| 2002/0123666 | A1 | 9/2002 | Matsumoto |
| 2002/0143326 | A1 | 10/2002 | Foley et al. |
| 2003/0028188 | A1 | 2/2003 | Paddock et al. |
| 2003/0120142 | A1 | 6/2003 | Dubuc et al. |
| 2003/0120144 | A1 | 6/2003 | Grabek et al. |
| 2003/0125719 | A1 | 7/2003 | Furnish |
| 2003/0208252 | A1 | 11/2003 | O'Boyle et al. |
| 2004/0073206 | A1 | 4/2004 | Foley et al. |
| 2004/0092806 | A1 | 5/2004 | Sagon et al. |
| 2004/0097788 | A1 | 5/2004 | Mourlas et al. |
| 2004/0138656 | A1 | 7/2004 | Francischelli et al. |
| 2004/0187875 | A1 | 9/2004 | He et al. |
| 2004/0215310 | A1 | 10/2004 | Amirana |
| 2004/0267326 | A1 | 12/2004 | Ocel et al. |
| 2005/0014995 | A1 | 1/2005 | Amundson et al. |
| 2005/0043637 | A1 | 2/2005 | Caplan et al. |
| 2005/0070987 | A1 | 3/2005 | Erickson |
| 2005/0075629 | A1 | 4/2005 | Chapelon et al. |
| 2005/0119523 | A1 | 6/2005 | Starksen et al. |
| 2005/0119548 | A1 | 6/2005 | Lin et al. |
| 2005/0197530 | A1 | 9/2005 | Wallace et al. |
| 2005/0197623 | A1 | 9/2005 | Leeflang et al. |
| 2005/0215899 | A1 | 9/2005 | Trahey et al. |
| 2005/0228452 | A1 | 10/2005 | Mourlas et al. |
| 2005/0251125 | A1 | 11/2005 | Pless et al. |
| 2005/0283195 | A1 | 12/2005 | Pastore et al. |
| 2006/0009756 | A1 | 1/2006 | Francischelli et al. |
| 2006/0013454 | A1 | 1/2006 | Flewelling et al. |
| 2006/0025760 | A1 | 2/2006 | Podhajsky |
| 2006/0089636 | A1 | 4/2006 | Christopherson et al. |
| 2006/0122583 | A1 | 6/2006 | Pesach et al. |
| 2006/0122587 | A1 | 6/2006 | Sharareh |
| 2006/0184048 | A1 | 8/2006 | Saadat |
| 2006/0229515 | A1 | 10/2006 | Sharareh et al. |
| 2006/0229594 | A1 | 10/2006 | Francischelli et al. |
| 2006/0278246 | A1 | 12/2006 | Eng et al. |
| 2007/0015964 | A1 | 1/2007 | Eversull et al. |
| 2007/0016079 | A1 | 1/2007 | Freeman et al. |
| 2007/0016130 | A1 | 1/2007 | Leeflang et al. |
| 2007/0038126 | A1 | 2/2007 | Pyle et al. |
| 2007/0049827 | A1 | 3/2007 | Donaldson et al. |
| 2007/0083217 | A1 | 4/2007 | Eversull et al. |
| 2007/0167828 | A1 | 7/2007 | Saadat |
| 2007/0179487 | A1 | 8/2007 | Tearney et al. |
| 2007/0185479 | A1 | 8/2007 | Lau |
| 2007/0225697 | A1 | 9/2007 | Shroff et al. |
| 2007/0270717 | A1 | 11/2007 | Tang et al. |
| 2007/0270789 | A1 | 11/2007 | Berger |
| 2007/0270792 | A1 | 11/2007 | Hennemann et al. |
| 2007/0270795 | A1 | 11/2007 | Francischelli et al. |
| 2007/0276259 | A1 | 11/2007 | Okawa et al. |
| 2007/0287886 | A1 | 12/2007 | Saadat |
| 2007/0293724 | A1 | 12/2007 | Saadat et al. |
| 2008/0009747 | A1 | 1/2008 | Saadat et al. |
| 2008/0015569 | A1 | 1/2008 | Saadat et al. |
| 2008/0021275 | A1 | 1/2008 | Tearney et al. |
| 2008/0033241 | A1 | 2/2008 | Peh et al. |
| 2008/0058650 | A1 | 3/2008 | Saadat et al. |
| 2008/0058785 | A1 | 3/2008 | Boyden et al. |
| 2008/0058786 | A1 | 3/2008 | Boyden et al. |
| 2008/0097476 | A1 | 4/2008 | Peh et al. |
| 2008/0101677 | A1 | 5/2008 | Mashke et al. |
| 2008/0103355 | A1 | 5/2008 | Boyden et al. |
| 2008/0119694 | A1 | 5/2008 | Lee |
| 2008/0125634 | A1 | 5/2008 | Ryan et al. |
| 2008/0154257 | A1 | 6/2008 | Sharareh et al. |
| 2008/0172049 | A1 | 7/2008 | Bredno et al. |
| 2008/0183036 | A1 | 7/2008 | Saadat et al. |
| 2008/0212867 | A1 | 9/2008 | Provenzano et al. |
| 2008/0214889 | A1 | 9/2008 | Saadat et al. |
| 2008/0221448 | A1 | 9/2008 | Khuri-Yakub et al. |
| 2008/0228032 | A1 | 9/2008 | Starksen et al. |
| 2008/0228079 | A1 | 9/2008 | Donaldson et al. |
| 2008/0243214 | A1 | 10/2008 | Koblish |
| 2008/0275300 | A1 | 11/2008 | Rothe et al. |
| 2008/0281293 | A1 | 11/2008 | Peh et al. |
| 2008/0300589 | A1 | 12/2008 | Paul et al. |
| 2009/0005771 | A1* | 1/2009 | Lieber ................ A61B 18/1492 600/549 |
| 2009/0012367 | A1 | 1/2009 | Chin et al. |
| 2009/0030276 | A1 | 1/2009 | Saadat et al. |
| 2009/0030412 | A1 | 1/2009 | Willis et al. |
| 2009/0054803 | A1 | 2/2009 | Saadat et al. |
| 2009/0062790 | A1 | 3/2009 | Malchano et al. |
| 2009/0076373 | A1 | 3/2009 | Maschke |
| 2009/0076375 | A1 | 3/2009 | Maschke |

(56) References Cited

U.S. PATENT DOCUMENTS

2009/0082623 A1 3/2009 Rothe et al.
2009/0082660 A1 3/2009 Rahn et al.
2009/0125022 A1 5/2009 Saadat et al.
2009/0131931 A1 5/2009 Lee et al.
2009/0143640 A1 6/2009 Saadat et al.
2009/0203962 A1 8/2009 Miller et al.
2009/0204069 A1 8/2009 Hirszowicz et al.
2009/0221871 A1 9/2009 Peh et al.
2009/0227999 A1 9/2009 Willis et al.
2009/0253991 A1 10/2009 Balas et al.
2009/0275799 A1 11/2009 Saadat et al.
2009/0281541 A1 11/2009 Ibrahim et al.
2009/0292211 A1 11/2009 Lin et al.
2009/0299354 A1 12/2009 Melsky et al.
2009/0299363 A1 12/2009 Saadat et al.
2009/0306643 A1 12/2009 Pappone et al.
2009/0326385 A1 12/2009 Hendriks et al.
2010/0022832 A1 1/2010 Makiyama
2010/0041986 A1 2/2010 Nguyen et al.
2010/0056966 A1 3/2010 Toth
2010/0081127 A1 4/2010 Maier et al.
2010/0081873 A1 4/2010 Tanimura et al.
2010/0081948 A1 4/2010 Pastore et al.
2010/0084563 A1 4/2010 Ohno
2010/0114094 A1 5/2010 Thapliyal et al.
2010/0130836 A1 5/2010 Malchano et al.
2010/0152728 A1 6/2010 Park et al.
2010/0198065 A1 8/2010 Thapliyal et al.
2010/0204544 A1 8/2010 Takei
2010/0204561 A1 8/2010 Saadat
2010/0228247 A1 9/2010 Paul et al.
2010/0241117 A1 9/2010 Paul et al.
2010/0274364 A1 10/2010 Pacanowsky
2010/0312094 A1 12/2010 Guttman et al.
2010/0312096 A1 12/2010 Guttman et al.
2010/0331838 A1 12/2010 Ibrahim et al.
2011/0009793 A1 1/2011 Lucero
2011/0019893 A1 1/2011 Rahn et al.
2011/0029058 A1 2/2011 Swanson
2011/0042580 A1 2/2011 Wilson et al.
2011/0066147 A1 3/2011 He et al.
2011/0071647 A1 3/2011 Mahon
2011/0082450 A1 4/2011 Melsky et al.
2011/0082451 A1 4/2011 Melsky et al.
2011/0082452 A1 4/2011 Melsky et al.
2011/0117025 A1 5/2011 Dacosta et al.
2011/0144524 A1 6/2011 Fish et al.
2011/0224494 A1 9/2011 Piskun et al.
2011/0230903 A1 9/2011 Bertolero
2011/0275932 A1 11/2011 Leblond et al.
2011/0276046 A1 11/2011 Heimbecher et al.
2011/0282250 A1 11/2011 Fung et al.
2011/0313417 A1 12/2011 De La Rama et al.
2012/0023638 A1 2/2012 Leicester
2012/0029504 A1 2/2012 Afonso et al.
2012/0109031 A1 5/2012 Vollbrecht
2012/0123276 A1 5/2012 Govari et al.
2012/0143177 A1 6/2012 Avitall
2012/0150046 A1 6/2012 Watson et al.
2012/0184812 A1 7/2012 Terakawa
2012/0184813 A1 7/2012 Terakawa
2012/0197243 A1 8/2012 Sherman et al.
2012/0215112 A1 8/2012 Lewis et al.
2012/0220999 A1 8/2012 Long
2012/0259263 A1 10/2012 Celermajer et al.
2012/0323237 A1 12/2012 Paul et al.
2012/0326055 A1 12/2012 Wilson et al.
2013/0006116 A1 1/2013 Kim et al.
2013/0023865 A1 1/2013 Steinke et al.
2013/0030425 A1 1/2013 Stewart et al.
2013/0079645 A1 3/2013 Amirana et al.
2013/0085416 A1 4/2013 Mest
2013/0096593 A1 4/2013 Thapliyal et al.
2013/0096594 A1 4/2013 Thapliyal et al.
2013/0102862 A1 4/2013 Amirana et al.
2013/0107002 A1 5/2013 Kikuchi
2013/0137949 A1 5/2013 Freeman et al.
2013/0150693 A1 6/2013 D'Angelo et al.
2013/0150732 A1 6/2013 Manzke et al.
2013/0158545 A1 6/2013 Govari et al.
2013/0172742 A1 7/2013 Rankin et al.
2013/0172875 A1 7/2013 Govari et al.
2013/0226163 A1 8/2013 Peled et al.
2013/0237841 A1 9/2013 Freeman et al.
2013/0253330 A1 9/2013 Demos
2013/0261455 A1 10/2013 Thapliyal et al.
2013/0267875 A1 10/2013 Thapliyal et al.
2013/0281920 A1 10/2013 Hawkins et al.
2013/0282005 A1 10/2013 Koch et al.
2013/0289358 A1 10/2013 Melsky et al.
2013/0289672 A1 10/2013 Hakomori et al.
2013/0296840 A1 11/2013 Condie et al.
2013/0310680 A1 11/2013 Werahera et al.
2013/0331831 A1 12/2013 Werneth et al.
2014/0031802 A1 1/2014 Melsky
2014/0058244 A1 2/2014 Krocak
2014/0058246 A1 2/2014 Boveja et al.
2014/0081253 A1 3/2014 Kumar et al.
2014/0088418 A1 3/2014 Radulescu et al.
2014/0107430 A1 4/2014 Deno et al.
2014/0121537 A1 5/2014 Aeby et al.
2014/0121660 A1 5/2014 Hauck
2014/0148703 A1 5/2014 Deladi et al.
2014/0163360 A1 6/2014 Stevens-Wright et al.
2014/0163543 A1 6/2014 Allison et al.
2014/0171806 A1 6/2014 Govari et al.
2014/0171936 A1 6/2014 Govari et al.
2014/0180273 A1 6/2014 Nair
2014/0194867 A1 7/2014 Fish et al.
2014/0194869 A1 7/2014 Leo et al.
2014/0243843 A1 8/2014 Havel et al.
2014/0275972 A1 9/2014 George et al.
2014/0276687 A1 9/2014 Goodman et al.
2014/0276771 A1 9/2014 Miller et al.
2014/0316280 A1 10/2014 Mueller et al.
2014/0324085 A1 10/2014 Thapliyal et al.
2014/0350547 A1 11/2014 Sharareh et al.
2014/0357956 A1 12/2014 Salahieh et al.
2014/0378843 A1 12/2014 Valdes et al.
2014/0378846 A1 12/2014 Hosoda et al.
2015/0038824 A1 2/2015 Lupotti
2015/0073245 A1 3/2015 Klimovitch et al.
2015/0099979 A1 4/2015 Caves et al.
2015/0141847 A1 5/2015 Sarvazyan et al.
2015/0148630 A1 5/2015 Meester
2015/0164332 A1 6/2015 Mercader et al.
2015/0182279 A1 7/2015 Ashton et al.
2015/0196202 A1 7/2015 Mercader et al.
2015/0216398 A1 8/2015 Yang et al.
2015/0327753 A1 11/2015 Amirana et al.
2015/0346100 A1 12/2015 Racowsky et al.
2015/0374217 A1 12/2015 Sinofsky
2016/0051321 A1 2/2016 Salahieh et al.
2016/0120599 A1 5/2016 Amirana et al.
2016/0120602 A1 5/2016 Ransbury et al.
2016/0143522 A1 5/2016 Ransbury et al.
2016/0228206 A1 8/2016 Bell et al.
2017/0014202 A1 1/2017 Ransbury et al.
2017/0020394 A1 1/2017 Harrington
2017/0035341 A1 2/2017 Nagale et al.
2017/0071664 A1* 3/2017 Lim .................... A61B 5/6857
2017/0135559 A1 5/2017 Horrisberger et al.
2017/0143420 A1* 5/2017 Sharareh ............ A61B 18/1492
2017/0164999 A1 6/2017 Hettel
2018/0263476 A1 9/2018 Amirana et al.
2019/0053849 A1 2/2019 Ransbury et al.
2019/0254735 A1 8/2019 Stewart et al.
2019/0262056 A1 8/2019 Yang et al.
2019/0350647 A1 11/2019 Ramberg et al.
2020/0008681 A1 1/2020 Sarvazyan
2020/0330727 A1 10/2020 Creighton
2020/0352425 A1 11/2020 Amirana et al.
2020/0352644 A1 11/2020 Ransbury et al.
2020/0352645 A1 11/2020 Amirana et al.

(56) References Cited

U.S. PATENT DOCUMENTS

| | | | |
|---|---|---|---|
| 2021/0045834 A1 | 2/2021 | Amirana et al. |
| 2021/0205017 A1 | 7/2021 | Amirana et al. |
| 2021/0369118 A1 | 12/2021 | Sarvazyan |
| 2022/0031377 A1 | 2/2022 | Ransbury et al. |
| 2022/0047150 A1 | 2/2022 | Wang et al. |
| 2022/0142482 A1 | 5/2022 | Mercader et al. |
| 2022/0226665 A1 | 7/2022 | Uto |
| 2023/0293000 A1 | 9/2023 | Amirana et al. |
| 2023/0404373 A1 | 12/2023 | Ransbury et al. |
| 2025/0127386 A1 | 4/2025 | Amirana et al. |

FOREIGN PATENT DOCUMENTS

| | | |
|---|---|---|
| CN | 101199410 | 6/2008 |
| CN | 102099671 | 6/2011 |
| CN | 102397104 | 4/2012 |
| CN | 203525125 | 4/2014 |
| CN | 106028914 | 10/2016 |
| DE | 102005021205 | 11/2006 |
| DE | 102011083522 | 3/2013 |
| EP | 2691041 | 2/2014 |
| EP | 2 889 013 | 7/2015 |
| JP | 60182928 | 9/1985 |
| JP | 63-262613 | 10/1988 |
| JP | 10150177 | 6/1998 |
| JP | 2006158546 | 6/2006 |
| JP | 20090148550 A | 7/2009 |
| JP | 2011/212423 | 10/2011 |
| JP | 201252882 A | 3/2012 |
| JP | 20130544551 A | 12/2013 |
| JP | 20150128586 A | 7/2015 |
| JP | 2018158114 A | 10/2018 |
| NL | 2002010 | 10/2009 |
| WO | WO 1997/037622 | 10/1997 |
| WO | WO 1999/013934 | 3/1999 |
| WO | WO 2001/001854 | 1/2001 |
| WO | WO 2001/072214 | 10/2001 |
| WO | WO 2003/092520 | 11/2003 |
| WO | WO 2004/028353 | 4/2004 |
| WO | WO 2006/028824 | 3/2006 |
| WO | 2006108143 A2 | 10/2006 |
| WO | 2007041542 A2 | 4/2007 |
| WO | WO 2007/109554 | 9/2007 |
| WO | WO 2007/127228 | 11/2007 |
| WO | WO 2008/028149 | 3/2008 |
| WO | 2008054423 A1 | 5/2008 |
| WO | WO 2008/114748 | 9/2008 |
| WO | WO 2008/154578 | 12/2008 |
| WO | WO 2010/075450 | 7/2010 |
| WO | WO 2011/025640 | 3/2011 |
| WO | WO 2011/113162 | 9/2011 |
| WO | WO 2012038824 | 3/2012 |
| WO | WO 2012/049621 | 4/2012 |
| WO | WO 2012/067682 | 5/2012 |
| WO | 20120131577 A2 | 10/2012 |
| WO | WO 2013/044182 | 3/2013 |
| WO | WO 2013/068885 | 5/2013 |
| WO | WO 2013/116316 | 8/2013 |
| WO | WO 2013/169340 | 11/2013 |
| WO | WO 2014/028770 | 2/2014 |
| WO | 2014205256 A2 | 12/2014 |
| WO | WO 2015/073871 | 5/2015 |
| WO | WO 2015/077474 | 5/2015 |
| WO | WO 2016/073476 | 5/2016 |
| WO | WO 2016/073492 | 5/2016 |
| WO | WO 2016/086160 | 6/2016 |
| WO | WO 2017/015257 | 1/2017 |

OTHER PUBLICATIONS

Anderson et al. "Real-time spectroscopic assessment of thermal damage: implications for radiofrequency ablation". J Gastrointest Surg. 2004; 8: 660-669.

Anderson, J.K., "Time Course of Nicotinamide Adenine Dinucleotide Diaphorase Staining after Renal Radiofrequency Ablation Influences Viability Assessment", Journal of Endourology, vol. 21, Issue 2, Mar. 5, 2007.

Asfour et al, "Signal decomposition of transmembrane voltage-sensitive dye fluorescence using a multiresolution wavelet analysis" IEEE Trans Biomed Eng. 2011; 58: 2083-2093.

Berthier, J.P., et al., "XeCl Laser Action at Medium Fluences on Biological Tissues: Fluorescence Study and Simulation with a Chemical Solution", Journal of Photochemistry and Photobiology B: Biology, vol. 5, Issues 3-4, pp. 495-503, May 1990.

Boersma et al.,."Pulmonary vein isolation by duty-cycled bipolar and unipolar radiofrequency energy with a multielectrode ablation catheter". Heart Rhythm5:1635-1642, 2008.

Bogaards et al., In Vivo Quantification of Fluorescent Molecular Markers in Real-Time: A Review to Evaluate the Performance of Five Existing Methods, Photodiagnosis and Photodynamic Therapy, vol. 4: 170-178 (2007).

Bogaards et al., n Vivo Quantification of Fluorescent Molecular Markers in Real-Time by Ratio Imaging for Diagnostic Screening and Image-Guided Surgery, Lasers in Surgery and Medicing vol. 39: 605-613 (2007).

Buch et al. "Epicardial catheter ablation of atrial fibrillation." Minerva Med. 2009; 100: 151-157.

Cancio et al., "Hyperspectral Imaging: A New Approach to the Diagnosis of Hemorrhagic Shock", The Journal of Trauma, 2006, vol. 60, No. 5: 1087-1095.

Chance et al, "Fluorescence measurements of mitochondrial pyridine nucleotide in aerobiosis and anaerobiosis" Nature. 1959; 184: 931-4.

Coremans et al, "Pretransplantation assessment of renal viability with NADH fluorimetry", Kidney International, vol. 57, (2000), pp. 671-683.

D'Avila A. "Epicardial catheter ablation of ventricular tachycardia." Heart Rhythm. 2008; 5: S73-5.

Demos et al, "Real time assessment of RF cardiac tissue ablation with optical spectroscopy", Opt Express. 2008; 16: 15286-15296.

Dickfeld et al, "Characterization of Radiofrequency Ablation Lesions With Gadolinium-Enhanced Cardiovascular Magnetic Resonance Imaging" J Am Coll Cardiol. 2006; 47: 370-378.

Dukkipati et al, "Visual balloon-guided point-by-point ablation: reliable, reproducible, and persistent pulmonary vein isolation", Circ Arrhythm Electrophysiol. 2010; 3: 266-273.

Dumas et al, "Myocardial electrical impedance as a predictor of the quality of RF-induced linear lesions." Physiol Meas. 2008; 29: 1195-1207.

Dyer, B., et al., Heart, "The Application of Autofluorescence Lifetime Metrology as a Novel Label-free Technique for the Assessment of Cardiac Disease", vol. 11, Issue Supplement 3, pp. 186, Jun. 2014.

Fleming et al, "Real-time monitoring of cardiac redio-frequency ablation lesion formation using an optical coherence tomography forward-imaging catheter", Journal of Biomedical Optics, May/Jun. 2010, vol. 15(3).

Fleming et al, "Toward guidance of epicardial cardiac radiofrequency ablation therapy using optical coherence tomography" J Biomed Opt. 2010; 15: 041510.

Girard et al, "Contrast-enhanced C-arm CT evaluation of radiofrequency ablation lesions in the left ventricle", JACC Cardiovasc Imaging. 2011; 4: 259-268.

Grimard et al, "Percutaneous epicardial radiofrequency ablation of ventricular arrhythmias after failure of endocardial approach: a 9-year experience" J Cardiovasc Electrophysiol. 2010; 21: 56-61.

Henz et al, "Simultaneous epicardial and endocardial substrate mapping and radiofrequency catheter ablation as first-line treatment for ventricular tachycardia and frequent ICD shocks in chronic chagasic cardiomyopathy" J Interv Card Electrophysiol. 2009; 26: 195-205.

Himel et al, "Translesion stimulus-excitation delay indicates quality of linear lesions produced by radiofrequency ablation in rabbit hearts", Physiol Meas. 2007; 28: 611-623.

(56) References Cited

OTHER PUBLICATIONS

Kalman, J.M., et al., "Cardiac Magnetic Resonance Imaging to Detect Non-Contiguous Scar Following Atrial Fibrillation Ablation: Identifying our Knowledge Gaps", European Heart Journal, Editorial, pp. 1-3, Feb. 26, 2014.
Kay et al, "Locations of ectopic beats coincide with spatial gradients of NADH in a regional model of low-flow reperfusion", Am J Physiol Heart Circ Physiol. 2008; 294: H2400-5.
Khoury et al., "Localizing and Quantifying Ablation Lesions in the Left Ventricle by Myocardial Contrast Echocardiography", J Cardiovasc Electrophysiol. 2004; 15: 1078-1087.
Kim et al, "Materials for multifunctional balloon catheters with capabilities in cardiac electrophysiological mapping and ablation therapy", Nat Mater. 2011; 10: 316-323.
Kistler, P.M., et al., "The Impact of CT Image Integration into an Electroanatomic Mapping System on Clinical Outcomes of Catheter Ablation of Atrial Fibrillation", Journal of Cardiovascular Electyrophysiology, vol. 17, Issue 10, pp. 1093-1101, Oct. 2006.
Lardo, et al "Visualization and temporal/spatial characterization of cardiac radiofrequency ablation lesions using magnetic resonance imaging", Circulation. 2000; 102: 698-705.
Li, "Multiphoton Microscopy of Live Tissues with Ultraviolet Autofluorescence", IEEE Journal of Selected Topic in Quantam Electronics , May/Jun. 2010, vol. 16, Issue 3, pp. 516-513.
Lo et al, "Three-dimensional electroanatomic mapping systems in catheter ablation of atrial fibrillation", Circ J. 2010; 74: 18-23.
Malchano, Z.J., "Integration of Cardiac CT/MR Imaging with Three-Dimensional Electroanatomical Mapping to Guide Catheter Manipulation in the Left Atrium: Implications for Catheter Ablation of Atrial Fibrillation", Journal of Cardiovascular Electrophysiology, vol. 17, Issue 11, pp. 1221-1229, Nov. 2006.
Mayevsky et al. "Oxidation-reduction states of NADH in vivo: from animals to clinical use", Mitochondrion. 2007; 7: 330-339.
Melby et al, "Atrial fibrillation propagates through gaps in ablation lines: implications for ablative treatment of atrial fibrillation", Heart Rhythm. 2008; 5: 1296-1301.
Menes et al, "Laparoscopy: searching for the proper insufflation gas" Surg Endosc. 2000; 14: 1050-1056.
Meng et al "A comparative study of fibroid ablation rates using radio frequency or high-intensity focused ultrasound", Cardiovasc Intervent Radiol. 2010; 33: 794-799.
Mercader et al, "NADH as an Endogenous Marker of Cardiac Tissue Injury at the Site of Radiofrequency Ablation", The George Washington University, Washington DC, Mar. 18, 2011.
Mercader et al, "Use of endogenous NADH fluorescence for real-time in situ visualization of epicardial radiofrequency ablation lesions and gaps", Am J Physiol Heart Circ Physiol, May 2012; 302(10): H2131-H2138.
Naito, H., et al., "Use of Nadh Fluorescence Imaging for Early Detection of Energy Failure and a Prediction of Infarction", Critical Care Medicine, vol. 39, Issue 12, pp. 40, Dec. 2011.
Nath et al, "Basic aspects of radiofrequency catheter ablation", J Cardiovasc Electrophysiol. 1994; 5: 863-876.
Niu et al, "An acute experimental model demonstrating 2 different forms of sustained atrial tachyarrhythmias". Circ Arrhythm Electrophysiol. 2009; 2: 384-392.
Perez et al. "Effects of gap geometry on conduction through discontinuous radiofrequency lesions" Circulation. 2006; 113: 1723-1729.
Ranji et al, "Fluorescence spectroscopy and imaging of myocardial apoptosis", Journal of Biomedical Optics 11(6), 064036 (Nov./Dec. 2006).
Ranji et al, "Quantifying Acute Myocardial Injury Using Ratiometric Fluorometry", IEEE Trans Biomed Eng. 2009, May 56(5): 1556-1563.
Riess et al, "Altered NADH and improved function by anesthetic and ischemic preconditioning in guinea pig intact hearts", Am J Physiol Heart Circ Physiol 283; H53-H60, Mar. 14, 2002.
Robertson, J.O., "Quantification of the Functional Consequences of Atrial Fibrillation and Surgical Ablation on the Left Atrium Using Cardiac Magnetic Resonance Imaging", European Journal of Cardio-Thoracic Surgery, vol. 46, Issue 4, pp. 720-728, Oct. 1, 2014.
Roger et al, "American Heart Association Stastics Committee and Stroke Subcommittee. Heart disease and stroke statistics—2011 update; a report from American Heart Association", Circulation 2011; 123: e18-e209.
Sethuraman et al., "Spectroscopic Intravascular Photoacoustic Imaging to Differentiate Atherosclerotic Plaques", Optics Express, vol. 16, No. 5, pp. 3362-3367, Mar. 3, 2008.
Smith, S., et al., "Imaging Appearances Following Thermal Ablation", Clinical Radiology, vol. 63, Issue 1, pp. 1-11, Jan. 2008.
Sosa et al, "Epicardial mapping and ablation techniques to control ventricular tachycardia". J Cardiovasc Electrophysiol. 2005; 16: 449-452.
Sra, J., et al., "Computed Tomography-Fluoroscopy Image Integration-Guided Catheter Ablation of Atrial Fibrillation", Journal of Cardiovascular Electrophysiology, vol. 18, Issue 4, pp. 409-414, Apr. 2007.
Swartling et al, "Changes in tissue optical properties due to radio-frequency ablation of myocardium", Med Biol Eng Comput. 2003; 41: 403-409.
Swift et al, "Controlled regional hypoperfusion in Langendorff heart preparations". Physiol Meas. 2008; 29: 269-79.
Swift, L.M., et al., "Properties of Blebbistatin for Cardiac Optical Mapping and Other Imaging Applications", European Journal of Physiology, vol. 464, Issue 5, pp. 503-512, Nov. 2012.
Swift, Luther Mitchell, "Real-Time Visualization of Cardiac Ablation Lesions Using Endogenous NADH Fluorescence and Reflected Light", A dissertation submitted to The Faculty of The Columbian College of Arts and Sciences of The George Washington University in partial fulfillment of the requirements for the degree of Doctor of Philosophy, Jul. 23, 2013.
Van Haesendonck C, Sinnaeve A, Willems R, Vandenbulcke F, Stroobandt R, ."Biophysical and electrical aspects of radiofrequency catheter ablation". Acta Cardiol 50: 105-115, 1995.
Vetterlein et al, "Extent of damage in aschemic, nonreperfused myocardium of anesthetized rats", Am J Physiol Heart Circ Physiol 285: H755-H765, 2003.
Vo-Dinh et al., "A Hyperspectral Imaging System for In Vivo Optical Diagnostics", IEEE Engineering in Medicine and Biology Magazine, pp. 40-49, Sep./Oct. 2004.
Weight, C.J., et al., "Correlation of Radiographic Imaging and Histopathology Following Cryoablation and Radio Frequency Ablation for Renal Tumors", The Journal of Urology, vol. 179, Issue 4, pp. 1277-1283, Apr. 2008.
Wu, H., et al., "Real-Time Monitoring of Radiofrequency Ablation and Postablation Assessment: Accuracy of Contrast-Enhanced US in Experimental Rat Liver Model", Radiology, vol. 270, No. 1, pp. 107-116, Jan. 2014.
Yokoyama et al, "Novel contact force sensor incorporated in irrigated radiofrequency ablation catheter predicts lesion size and incidence of steam pop and thrombus", Circ Arrhythm Electrophysiol. 2008; 1: 354-362.
Zuzak et al., "Characterization of a Near-Infrared Laparoscopic Hyperspectral Imaging System for Minimally Invasive Surgery", Analytical Chemistry, vol. 79, No. 12, pp. 4709-4715, Jun. 15, 2007.

* cited by examiner

SYSTEMS AND METHODS FOR OPTIMIZING TISSUE ABLATION

RELATED APPLICATIONS

This application claims the benefit of and priority to U.S. Provisional Application Ser. No. 63/110,135, filed on Nov. 5, 2020, which is incorporated herein by reference in its entirety.

FIELD

The present disclosure generally relates to catheters, and more particularly ablation and visualization catheters.

BACKGROUND

Ablation therapy is a minimally invasive procedure that applies energy to tissue to cause cell death. For example, ablation therapy can be used to remove or destroy abnormal tissue types (for example, tumors). Another example is the use of ablation therapy to treat atrial fibrillation (AF). It can be necessary to adjust various ablation parameters to ensure proper and complete ablation of the target tissue without over-ablating the area and destroying healthy tissue. There is a thus need for system and method to optimize tissue ablation.

SUMMARY

In some embodiments, the present disclosure provides systems and methods for improved tissue ablation.

In some aspects, a catheter system is provided for determining tissue thickness, including a catheter including a catheter body and a distal tip positioned at a distal end of the catheter body; one or more source openings in the distal tip for passing light energy to a tissue; one or more detector openings in the distal tip for passing light energy from the tissue; and a visualization system including a light source, a light measuring instrument, and one or more optical fibers in communication with the light source and the light measuring instrument and extending through the catheter body to the distal tip, the one or more optical fibers including one or more source fibers to pass light energy to the tissue through the one or more source openings and one or more detector fibers to detect light energy from the tissue through the one or more detector openings, wherein a distal end of the one or more source fibers is positioned at the one or more source openings and a distal end of the one or more detector fibers is positioned at the one or more detector openings, the one or more source openings and the one or more detector openings being aligned in a longitudinal arrangement along a length of the distal tip and being paired and spaced apart from one another by a separation distance calculated based on a thickness of the tissue to be measured.

In some embodiments, the light energy for illuminating the tissue has at least one wavelength between about 750 nm and about 1400 nm. In some embodiments, the separation distance between a source opening and a detector opening is proportional to the thickness of the tissue. In some embodiments, the separation distance between a source opening and a detector opening is in a range of 1 to 15 mm. In some embodiments, the catheter system, can also include a processor in communication with the light measuring instrument, the processor being programmed to determine a thickness of the tissue using information from the one or more detector fibers and the separation distance between the one or more source fibers and the one or more detector fibers. In some embodiments, the one or more source openings and the one or more detector openings are disposed circumferentially along the distal tip. In some embodiments, multiple detector openings are aligned with and positioned at different distances from a corresponding source opening of the one or more source openings. In some embodiments, the one or more source openings and the one or more detector openings are positioned in an electrode ring, the electrode ring being configured to function as an electrode to determine contact between the electrode ring and the tissue.

In some embodiments, the catheter system can also include an ablation element configured to deliver ablation energy to the tissue. The ablation energy can be selected from a group consisting of pulsed field ablation energy, electroporation energy, radiofrequency (RF) energy, microwave energy, electrical energy, electromagnetic energy, cryoenergy, laser energy, ultrasound energy, acoustic energy, chemical energy, thermal energy and combinations thereof.

In some aspects, a catheter system can be provided for determining tissue thickness, including a catheter including a catheter body and a distal tip positioned at a distal end of the catheter body; one or more source openings in the distal tip for passing light energy to a tissue; one or more detector openings in the distal tip for passing light energy from the tissue, the one or more source openings and the one or more detector openings being aligned in a longitudinal arrangement along a length of the distal tip and being paired and spaced apart from one another by a separation distance calculated based on a thickness of the tissue to be measured; one or more source fibers having a distal tip disposed at one or more source openings and being configured to pass light energy to the tissue through the one or more source openings; and one or more detector fibers having a distal tip disposed at the one or more detector openings and being configured to detect light energy from the tissue through the one or more detector openings.

In some embodiments, the catheter system can further include an ablation element configured to deliver ablation energy to the tissue. The ablation energy can be selected from a group consisting of pulsed field ablation energy, electroporation energy, radiofrequency (RF) energy, microwave energy, electrical energy, electromagnetic energy, cryoenergy, laser energy, ultrasound energy, acoustic energy, chemical energy, thermal energy and combinations thereof.

In some aspects, a system can be provided for determining tissue thickness, including a catheter including a catheter body and a distal tip positioned at a distal end of the catheter body; one or more source openings in the distal tip for passing light energy to a tissue; one or more detector openings in the distal tip for passing light energy from the tissue; a visualization system including a light source, a light measuring instrument, and one or more optical fibers in communication with the light source and the light measuring instrument and extending through the catheter body to the distal tip, the one or more optical fibers including one or more source fibers to pass light energy to the tissue through the one or more source openings and one or more detector fibers to detect light energy from the tissue through the one or more detector openings; and a processor in communication with the light measuring instrument, the processor being programmed to determine a thickness of the tissue using information from the one or more detector fibers and a distance between the one or more source fibers and the one or more detector fibers, wherein the thickness of the tissue is used to determine one or more ablation parameters, wherein a distal end of the one or more source fibers is positioned at the one or more source openings and a distal end of the one or more detector fibers is positioned at the one or more detector openings, the one or more source openings and the one or more detector openings being aligned in a longitudinal arrangement along a length of the distal tip and being paired and spaced apart from one another by a separation distance calculated based on a thickness of the tissue to be measured.

In some embodiments, the light energy for illuminating the tissue has at least one wavelength between about 750 nm and about 1400 nm. In some embodiments, the separation distance between a source opening and a detector opening is proportional to the thickness of the tissue. In some embodiments, the separation distance between a source opening and a detector opening is in a range of 1 to 15 mm. In some embodiments, the one or more source openings and the one or more detector openings are disposed circumferentially along the distal tip. In some embodiments, multiple detector openings are aligned with and positioned at different distances from the one or more source openings. In some embodiments, the one or more source openings and the one or more detector openings are positioned in an electrode ring, the electrode ring being configured to function as an electrode to determine contact between the electrode ring and the tissue.

In some embodiments, the system can further include an ablation element configured to deliver ablation energy to the tissue. The ablation energy can be selected from a group consisting of pulsed field ablation energy, electroporation energy, radiofrequency (RF) energy, microwave energy, electrical energy, electromagnetic energy, cryoenergy, laser energy, ultrasound energy, acoustic energy, chemical energy, thermal energy and combinations thereof.

In some aspects, a method can be provided for determining tissue thickness, including advancing a catheter to a tissue, the catheter including a catheter body; a distal tip positioned at a distal end of the catheter body, the distal tip having one or more source openings for passing light energy to a tissue and one or more detector openings for passing light energy from the tissue; and one or more optical fibers extending through the catheter body and including one or more source fibers to pass light energy to the tissue through the one or more source openings and one or more detector fibers to detect light energy from the tissue through the one or more detector openings, the one or more source openings and the one or more detector openings being aligned in a longitudinal arrangement along a length of the distal tip and being paired and spaced apart from one another by a separation distance calculated based on a thickness of the tissue to be measured; illuminating the tissue through the one or more source openings in the distal tip of the catheter using the one or more source fibers; collecting light reflected from the tissue through the one or more detector openings from the one or more detector fibers and directing the collected light to a light measuring instrument; determining a thickness of the tissue using the collected light from the one or more detector openings; and determining one or more ablation parameters using the thickness of the tissue.

In some embodiments, the light energy for illuminating the tissue has at least one wavelength between about 750 nm and about 1400 nm. In some embodiments, the separation distance between a source opening and a detector opening is proportional to the thickness of the tissue. In some embodiments, the separation distance between a source opening and a detector opening is in a range of 1 to 15 mm. In some embodiments, the method can further include delivering ablation energy to the tissue, wherein the ablation energy is selected from a group consisting of pulsed field ablation energy, electroporation energy, radiofrequency (RF) energy, microwave energy, electrical energy, electromagnetic energy, cryoenergy, laser energy, ultrasound energy, acoustic energy, chemical energy, thermal energy and combinations thereof.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

Figure 1:
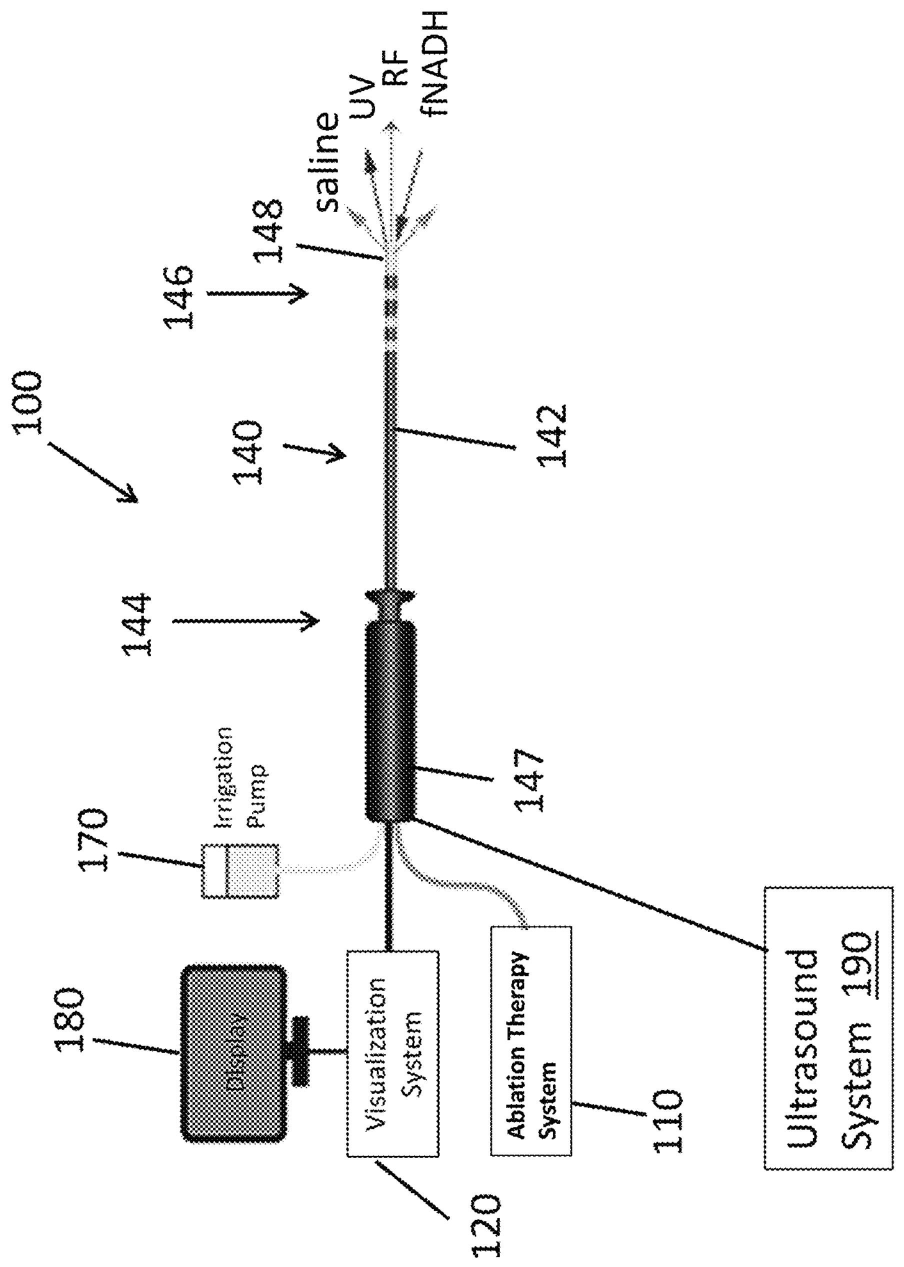
FIG. 1 is an embodiment of an ablation visualization system of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The systems and methods of the present disclosure may be used to measure the thickness of the tissue to aid in the ablation of the tissue. Knowing the wall thickness and the lesion depth progression, in real time, can help the physician to form lesions that are complete (i.e., transmural). Transmural lesions are effective at blocking the unwanted electrical propagation of cardiac arrhythmias. Lesions that are too shallow (i.e., non-transmural) may look complete from the surface of the myocardium in contact with the catheter, due to low voltage on the electrogram but be conducting beyond the lesion depth. Lesions that are too deep (i.e., beyond transmural) may damage extra-cardiac structures such as the esophagus or vagus nerve. For example, damaging the esophagus can be fatal to the patient. Due to the depth of penetration of the illuminating wavelength, there may be increased sensitivity to tissue composition.

According to some aspects of the present disclosure, there is provided a system for visualizing ablated tissue comprising a catheter having one or more source-detector pairs; one or more light sources configured to output light having a wavelength between 750-1200 nm for measuring the heart wall thickness and between 300 and 500 nm for exciting NADH fluorescence; a light measuring instrument; and one or more optical fibers in communication with the light source and the light measuring instrument and extending through the catheter body to the source-detector pairs, wherein the one or more optical fibers are configured to pass light energy from the light source to the light directing member for illuminating tissue outside the distal tip and the one or more optical fibers are configured to relay light energy reflected from the tissue to the light measuring instrument.

In some embodiments, the instant systems and methods can be used to determine heart wall thickness. For example, time and frequency domain methods can be applied in determining heart wall thickness. In some embodiments, the source-detector (SD) distance combinations are specific to a balance of being able to measure heart wall thickness domains while achieving practical contact for the fibers. The SD pairs can have contact with the myocardial surface to make the measurement. In some embodiments, the SD distance is typically 2 times the maximum desired depth of measurement. In some embodiments, the SD distance is in the range of 0 to 15 mm.

In some embodiments, limiting the effective range of the measurement increases its depth resolution. For example, human atria are usually less than 6 mm and the SD distances can be optimized for resolution over the practical range (2 to 6 mm) for atrial applications. A different (i.e. greater) SD distance can optimize measurements for the ventricles (6 mm to >10 mm). The instant systems and methods can be optimized for the appropriate heart chamber by changing the SD distance. For example, larger SD separation can be employed for the ventricles, and smaller SD distances for the atria.

In some embodiments, adding apriori knowledge can enhance the measurement performance. If known information can be fed into the algorithm, the performance increases. Examples include: Knowing which heart chamber (atria thinner); Using fluorescence to detect the presence or lack of collagen. Knowing the orientation of the catheter and therefore knowing the extra-cardiac structure, for example, the optical properties of lung tissue are very different than esophageal tissue, which is muscular like the heart. Adding this to the machine-learning model improved performance in the simulations.

In some embodiments, the catheters of the present disclosure are provided with optical means to measure wall thickness prior to or during cardiac ablation. In some embodiments, the instant systems can measure the wall thickness, and also track lesion progression. In some embodiments, the instant systems can determine the tissue thickness over a range of physiological variations, especially collagen and fat presence in an otherwise healthy myocardium.

The present disclosure further provides systems and methods for applying radiofrequency, pulsed field modulated, laser or cryo ablation energy to the body to form therapeutic lesions. In some embodiments, the systems and methods of the present disclosure can be employed for imaging tissue using nicotinamide adenine dinucleotide hydrogen (NADH) fluorescence (fNADH). By way of a non-limiting example, the present systems and methods can be used in connection with the treatment of Atrial Fibrillation (AF). In general, the system can include a catheter with an optical system for exchanging light between tissue and the catheter. The fluorescence signature returned from the tissue can be used to determine the presence or absence of ablation lesions in illuminated tissue as well as information about a lesion as it is forming during ablation. This optical tissue interrogation can be performed on various tissue types, including, without limitation, various cardiac tissues, endocardial tissue, epicardial tissue, myocardium tissue, valves, vascular structures, and fibrous and anatomical structures. The systems and methods of the present disclosure may be used to analyze tissue composition including, but not limited to the presence of collagen and elastin. However, the presently disclosed methods and systems may also be applicable for analyzing lesions in other tissue types, for example, skeletal muscle, liver, kidney, pancreas, brain, neural tissue, spleen, breast, uterus, cervical, prostate, bladder, esophagus, lung, pulmonary, arterial, blood clot or hematologic, gastrointestinal tract, adrenals, ovaries, testicles, and genitourinary tissue. For example, the systems and methods described herein can also be used in urological applications, such as for ablation of kidney to treat kidney cancer. The lesions to be analyzed may be created by application of ablation energy during the ablation procedure. In some embodiments, existing lesions, created by ablation or by other means, may also be analyzed using methods and systems disclosed herein.

In reference to FIG. 1, the system for providing ablation therapy 100 may include an ablation therapy system 110, a visualization system 120, and a catheter 140. In some embodiments, the system 100 may also include an irrigation system 170. The system may also include a display 180, which can be a separate display or a part of the visualization system 120, as described below.

In some embodiments, the ablation therapy system 110 is designed to supply ablation energy to the catheter 140. The ablation therapy system 110 may include one or more energy sources that can generate radiofrequency (RF) energy, microwave energy, electrical energy (for example, pulsed field ablation), electroporation, electromagnetic energy, cryoenergy, laser energy, ultrasound energy, acoustic energy, chemical energy, thermal energy or any other type of energy that can be used to ablate tissue.

In some embodiments, the system includes an RF generator, an irrigation pump 170, an irrigated-tip ablation catheter 140, and the visualization system 120.

Light Source and Light Measurement Device

Figure 2A:
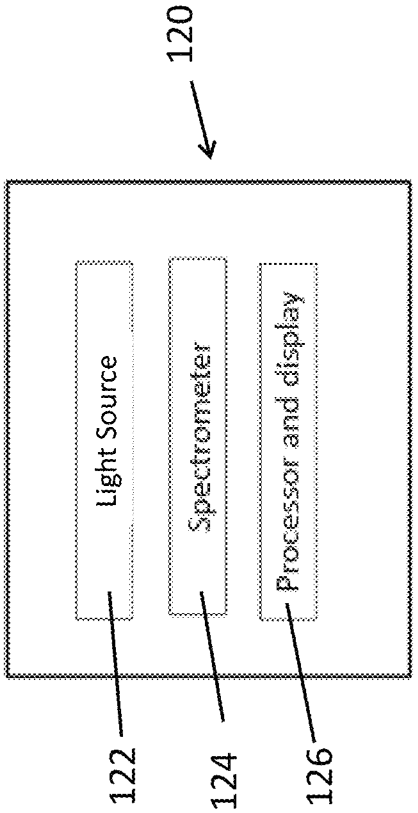
FIG. 2A is a diagram of an embodiment of a visualization system for use in connection with an ablation visualization system of the present disclosure.

In reference to FIG. 2A, the visualization system 120 may include a light source 122, a light measuring instrument 124, and a computer system 126.

Figure 2B:
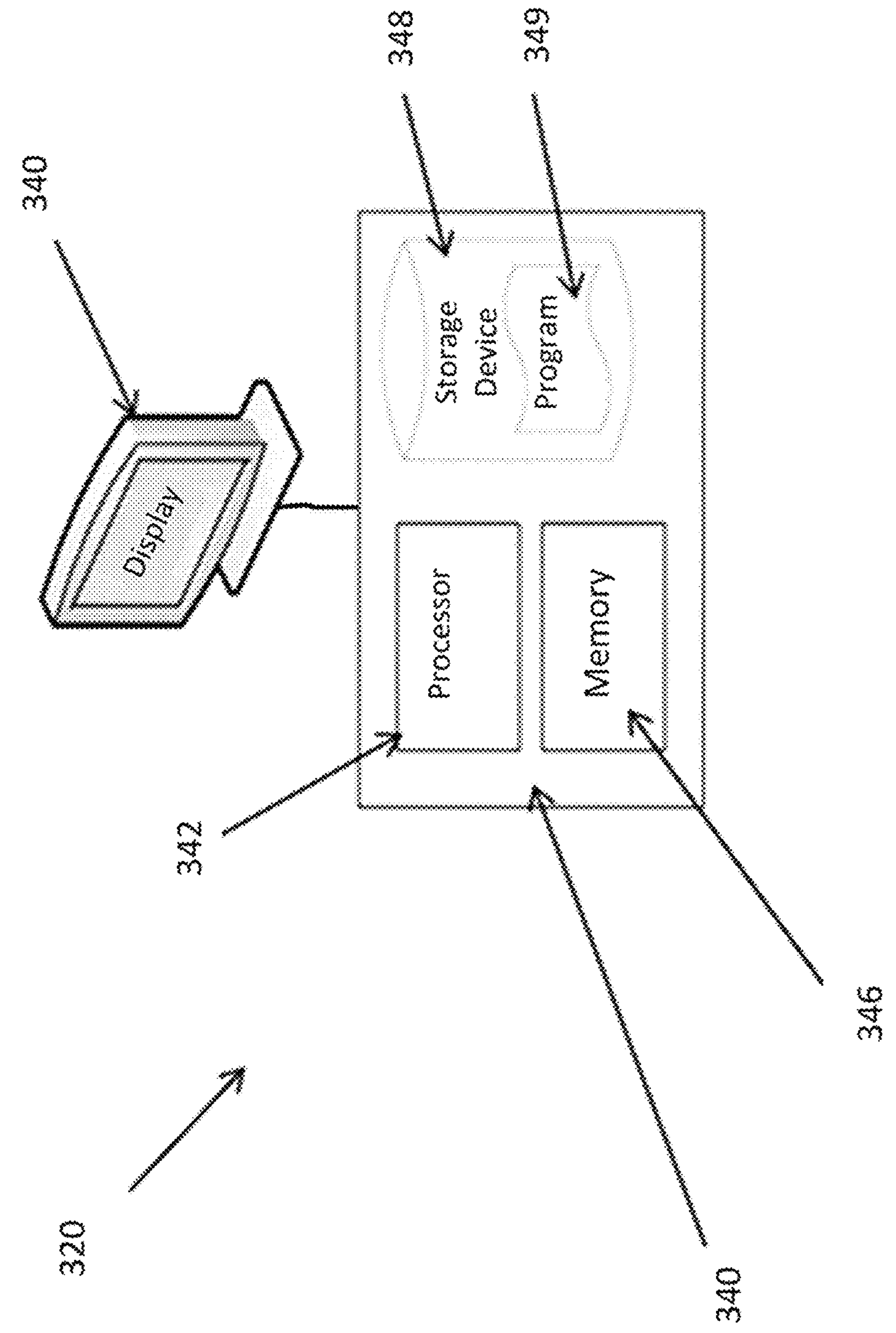
FIG. 2B illustrates an exemplary computer system suitable for use in connection with the systems and methods of the present disclosure.

The computer system 126 can be programed to control various modules of the system 100, including, for example, control over the light source 122, control over the light measuring instrument 124, execution of application specific software, control over ultrasound, navigation and irrigation systems and similar operations. FIG. 2B shows, by way of example, a diagram of a typical processing architecture 320, which may be used in connection with the methods and systems of the present disclosure. A computer processing device 340 can be coupled to display 340AA for graphical output. Processor 342 can be a computer processor 342 capable of executing software. Typical examples can be computer processors (such as Intel® or AMD® processors), ASICs, microprocessors, and the like. Processor 342 can be coupled to memory 346, which can be typically a volatile RAM memory for storing instructions and data while processor 342 executes. Processor 342 may also be coupled to storage device 348, which can be a non-volatile storage medium, such as a hard drive, FLASH drive, tape drive, DVDROM, or similar device. Although not shown, computer processing device 340 typically includes various forms of input and output. The I/O may include network adapters, USB adapters, Bluetooth radios, mice, keyboards, touchpads, displays, touch screens, LEDs, vibration devices, speakers, microphones, sensors, or any other input or output device for use with computer processing device 340. Processor 342 may also be coupled to other types of computer-readable media, including, but not limited to, an electronic, optical, magnetic, or other storage or transmission device capable of providing a processor, such as the processor 342, with computer-readable instructions. Various other forms of computer-readable media can transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Program 349 can be a computer program or computer readable code containing instructions and/or data and can be stored on storage device 348. The instructions may comprise code from any computer-programming language, including, for example, C, C++, C#, Visual Basic, Java, Python, Perl, and JavaScript. In a typical scenario, processor 342 may load some or all of the instructions and/or data of program 349 into memory 346 for execution. Program 349 can be any computer program or process including, but not limited to web browser, browser application, address registration process, application, or any other computer application or process. Program 349 may include various instructions and subroutines, which, when loaded into memory 346 and executed by processor 342 cause processor 342 to perform various operations, some or all of which may effectuate the methods for managing medical care disclosed herein. The program 349 may be stored on any type of non-transitory computer readable medium, such as, without limitation, hard drive, removable drive, CD, DVD or any other type of computer-readable media.

In some embodiments, the computer system may be programmed to perform the steps of the methods of the present disclosure and control various parts of the instant systems to perform necessary operation to achieve the methods of the present disclosure. In some embodiments, the processor may be programed to receive NADH fluorescence data from a tissue illuminated with UV light through the distal tip of the catheter, wherein the tissue is illuminated in a radial direction, an axial direction, or both; to determine from a level of NADH fluorescence in the illuminated tissue when the distal tip of the catheter is in contact with the tissue; and to cause (either automatically or by prompting the user) delivery of ablation energy to the tissue to form a lesion in the tissue upon determining that the distal tip is in contact with the tissue.

The processor may further be programmed for monitoring the level of NADH fluorescence during the delivering ablation energy to confirm that the distal tip remains in contact with the tissue. In some embodiments, monitoring the level of NADH fluorescence during the delivery of ablation energy may be utilized to determine stability of contact between the distal tip and the tissue. In some embodiments, ablation of the tissue may be stopped when the contact between the distal tip and the tissue is not stable. In some embodiments, the processor may further be programmed to collect a spectrum of fluorescence light returned from the illuminated tissue to distinguish tissue type.

In some embodiments, in order to measure cardiac wall thickness and track lesion progression, more than one wavelength of light can be used. In some embodiments, the light source 122 may output light in a range sufficient to excite one or more fluorophores in the tissue (for example, NADH). In some embodiments, the light source produces light with an output wavelength within the target fluorophore (NADH, in some embodiments) absorption range in order to induce fluorescence in healthy myocardial cells. In some embodiments, such fluorophore excitation wavelength is between 350 and 500 nm. In some embodiments, the wavelength may be 375 nm+/−50 nm. The output power of the light source 122 may be high enough to produce a recoverable tissue fluorescence signature, yet not so high as to induce cellular damage. The light source 122 may be coupled to an optical fiber to deliver light to the catheter 140, as will be described below.

In some embodiments, the light source 122 can also provide different wavelengths of light that can be used to determine wall thickness, and needs to be at a longer wavelength than the wavelength of light to track lesion progression to ensure depth of penetration at distances amenable to cardiac wall thickness ranges. In some embodiments, this additional light can be in the near infrared wavelength range, which is between 750-2500 nm. However, wavelengths starting at about 1,400 nm and above are absorbed by water and not useful for wall measurement. This means that the practical range for measuring the heart wall thickness is between 750-1400 nm.

Various light sources can be used, either a single light source with an output in both the NADH excitation range and wall thickness measurement range, or multiple light sources for the different ranges. Thus, in some embodiments, the light source 122 is configured to emit multiple wavelength of light, and in some embodiment, the light source 122 includes multiple light sources with each source emitting a different wavelength of light. In some embodiments, the light sources 122 can be lasers. LED light sources are an alternative to lasers but have limitations when used in catheter-based implementations. First, low LED power, relative to lasers, may be a limiting factor due to optical coupling inefficiencies in getting the light focused on the optical fiber. Second, LED output can be wide band and overlap with the response wavelengths making the tissue response very difficult to detect. Laser-generated light may provide much more power for illumination and may be more efficiently coupled into a fiber-based illumination system, as is used in some embodiments of the catheter. In some embodiments, the instant system can use a laser with adjustable power up to 150 mW. In some embodiments, the light source 122 is a solid-state laser that can generate UV light to excite NADH fluorescence.

In some embodiments, the systems of the present disclosure may utilize a spectrometer as the light measuring instrument 124. In some embodiments with multiple fibers or an imaging bundle, the light measuring instrument 124 may comprise a camera connected to the computer system 126 for analysis and viewing of tissue fluorescence. In some embodiments, the camera may have high quantum efficiency for wavelengths corresponding to NADH fluorescence. One such camera is an Andor iXon DV860. The spectrometer 124 may be coupled to an imaging bundle that can be extended into the catheter 140 for visualization of tissue. In some embodiments, the imaging bundle for spectroscopy and the optical fiber for illumination may be combined. An optical bandpass filter of between 435 nm and 485 nm, in some embodiments, of 460 nm, may be inserted between the imaging bundle and the camera to block light outside of the NADH fluorescence emission band. In some embodiments, other optical bandpass filters may be inserted between the imaging bundle and the camera to block light outside of the NADH fluorescence emission band selected according to the peak fluorescence of the tissue being imaged.

In some embodiments, the light measuring instrument 124 may be a CCD (charge-coupled device) camera. In some embodiments, the spectrometer 124 may be selected so it is capable of collecting as many photons as possible and that contributes minimal noise to the image. Usually for fluorescence imaging of live cells, CCD cameras should have a quantum efficiency at about 460 nm of at least between 50-70%, indicating that 30-50% of photons will be disregarded. In some embodiments, the camera has quantum efficiency at 460 nm of about 90%. The camera may have a sample rate of 80 KHz. In some embodiments, the spectrometer 124 may have a readout noise of 8 e− (electrons) or less. In some embodiments, the spectrometer 124 has a minimum readout noise of 3e−. Other light measuring instruments may be used in the systems and methods of the present disclosure.

Figure 9:
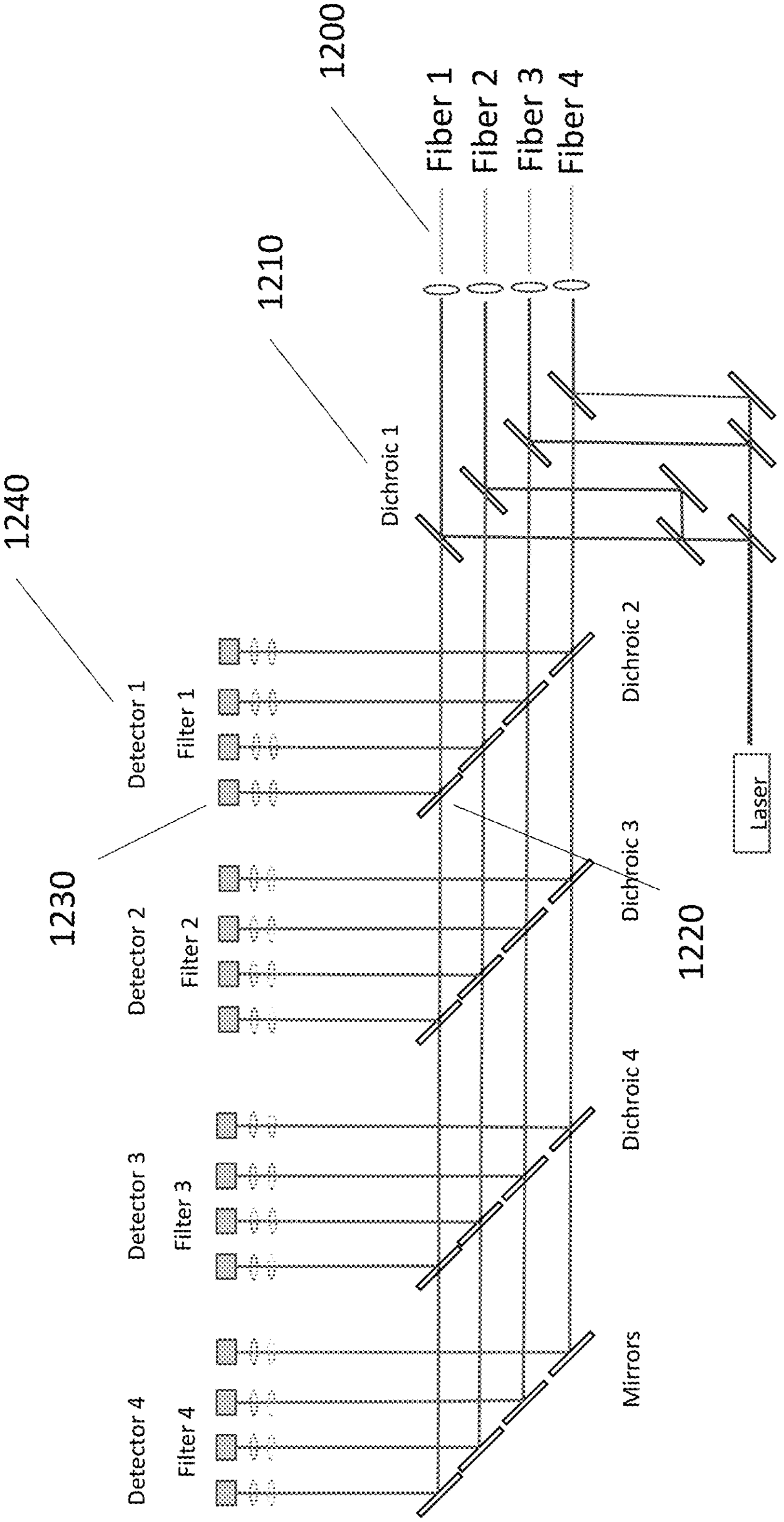
FIG. 9 is an exemplary schematic diagram of an optical filter matrix providing discrete optical bands of sensitivity.

In applications where the tissue-response information is in particular bands of interest, such as with NADH fluorescence (400 nm to 600 nm) and cardiac wall thickness measurement (700 nm to 1200 nm), the spectrometer can be replaced by discrete narrow-band detectors. FIG. 9 shows an embodiment of a 4-fiber system with 4 discrete optical detectors. Each detector is responsible for the particular wavelengths of interest. Information outside the bands of interest can be ignored or not detected. Tracing the optical pathway of Fiber 1 1200, the light from this detector passes through dichroic mirror 1 1210 and is reflected by dichroic mirror set 2 1220 towards filter set 1 1230. The light passing through the filter 1230 is directed to the detector 1 1240 for digitization. This architecture is repeated in parallel in the diagram for fibers 2, 3, and 4 and could be replicated as many times as necessary.

In some embodiments, the discrete detectors, as shown in FIG. 9, can be optimized for the particulars of the response either increased sensitivity for very low light responses (NADH) or increased speed that is required of wall thickness measurement. An additional detector can be used for detecting room light that could indicate that the catheter is not in the body and the laser can be disabled to either prolong the laser's useful life or as a safety mechanism to disable the laser when not in the body to limit laser light exposure for the physician, or both.

The optical fiber 150 can deliver from the light source to the tissue and to deliver the light gathered from the tissue the light measuring instrument 124. The computer system 126 acquires the information from the light measuring instrument 124 and displays it to the physician. In some embodiments, the computer 126 can also provide several additional functions, such as, for example, control over the light source 122, control over the light measuring instrument 124, ablation system 110, other subsystems of the system 100 and/or execution of application specific software.

In some embodiments, the light reflected from the tissue can be used to determine the thickness of the tissue as described in more detail below. In some embodiments, the computer 126 will also analyze the fluorescence from one or more fluorophores in the tissue, to gain understanding of one or more properties of the tissue.

In some embodiments, the system 100 of the present disclosure may further include an ultrasound system 190. The catheter 140 may be equipped with ultrasound transducers in communication with the ultrasound system. In some embodiments, the ultrasound may show tissue depths, which in combination with the metabolic activity or the depth of lesion may be used to determine if a lesion is in fact transmural or not.

Catheter

Referring back to FIG. 1, the catheter 140 includes a catheter body 142 having a proximal end 144 and a distal end 146. The catheter body 142 may be made of a biocompatible material, and may be sufficiently flexible to enable steering and advancement of the catheter 140 to a site of ablation. In some embodiments, the catheter body 142 may have zones of variable stiffness. For example, the stiffness of the catheter 140 may increase from the proximal end 144 toward the distal end 146. In some embodiments, the stiffness of the catheter body 142 is selected to enable delivery of the catheter 140 to a desired cardiac location. In some embodiments, the catheter 140 can be a steerable, irrigated radiofrequency (RF) ablation catheter that can be delivered through a sheath to the endocardial space, and in the case of the heart's left side, via a standard transseptal procedure using common access tools. The catheter 140 may include a handle 147 at the proximal end 144. The handle 147 may be in communication with one or more lumens of the catheter to allow passage of instruments or materials through the catheter 140. In some embodiments, the handle 147 may include connections for the standard RF generator and irrigation system for therapy.

Figure 3:
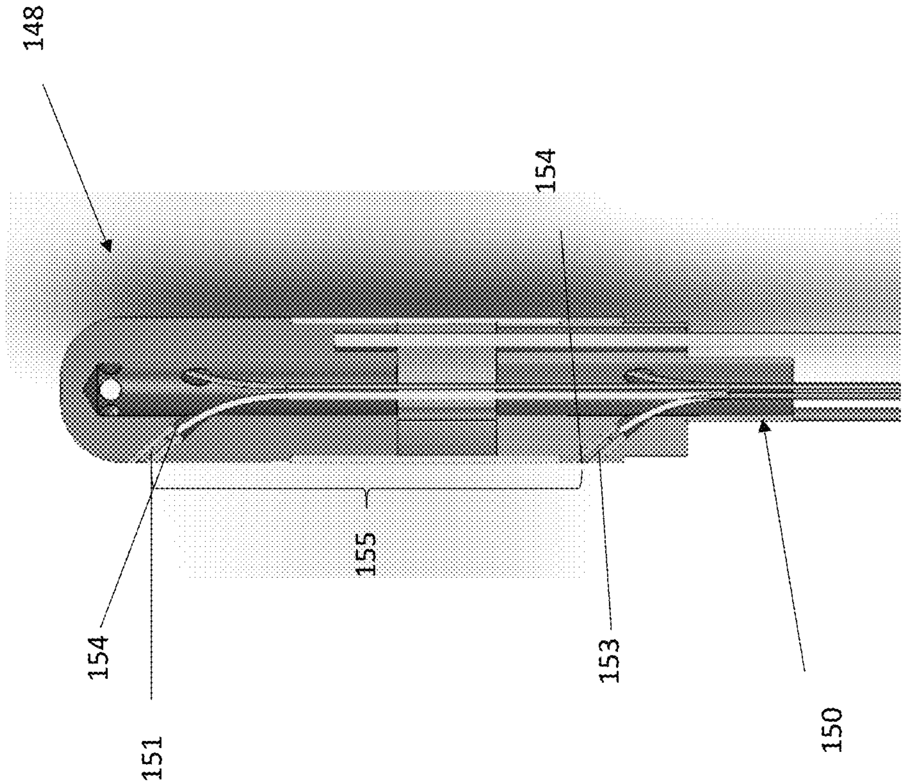
FIG. 3 illustrates an embodiment of a cross-sectional view of a distal end of a catheter of the present disclosure.
Figure 4:
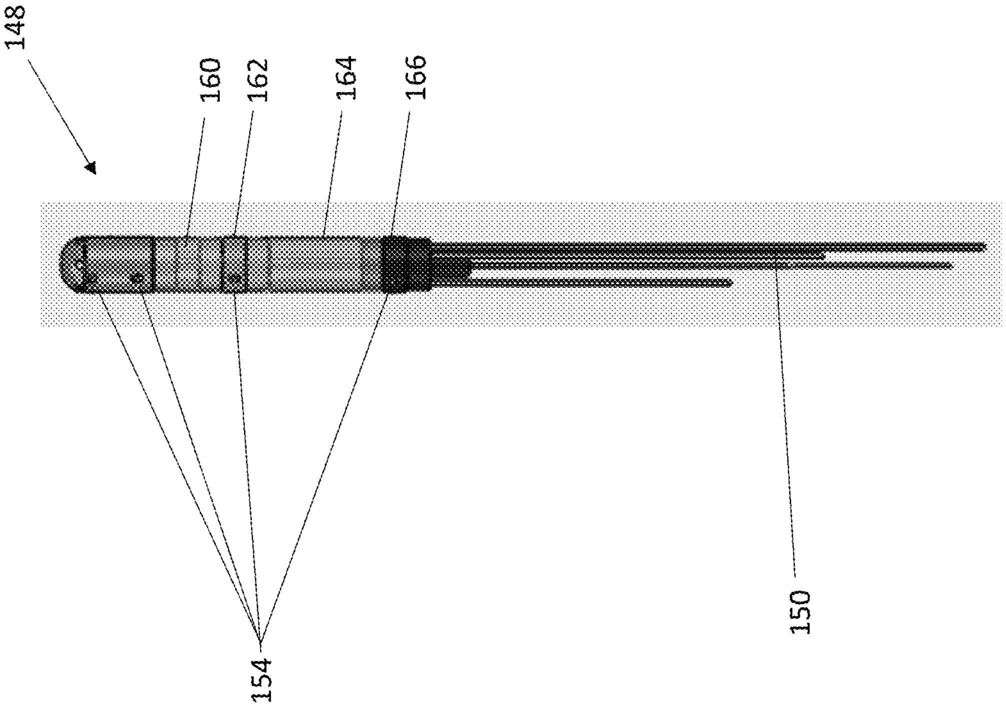
FIG. 4 illustrates an embodiment of a distal end of a catheter of the present disclosure.

FIG. 3 and FIG. 4 illustrates a detailed view of the distal tip 148. In some embodiments, the distal tip 148 may be configured to act as an electrode for diagnostic purposes, such as electrogram sensing, for therapeutic purposes, such as for emitting ablation energy, or both. In some embodiments where ablation energy is required, the distal tip 148 of the catheter 140 could serve as an ablation electrode or ablation element.

In the embodiments where RF energy is implemented, the wiring to couple the distal tip 148 to the RF energy source (external to the catheter) can be passed through a lumen of the catheter. The distal tip 148 may include a port in communication with the one or more lumens of the catheter. The distal tip 148 can be made of any biocompatible material. In some embodiments, if the distal tip 148 is configured to act as an electrode, the distal tip 148 can be made of metal, including, but not limited to, platinum, platinum-iridium, stainless steel, titanium or similar materials.

In reference to FIG. 3 and FIG. 4, optical fibers or an imaging bundle 150 may be passed from the visualization system 120, through the catheter body 142, and into the distal tip 148. The distal tip 148 can be provided with one or more openings 154 for exchange of light energy between the optical fibers 150 and tissue. The light energy can be delivered from the light source by one or more fibers 150 to the distal tip 148, where it illuminates the tissue in the proximity of the distal tip 148. This illumination light is either reflected or causes the tissue to fluoresce. The light reflected by and fluoresced from the tissue may be gathered by the optical fibers 150 within the distal tip 148 and carried back to the visualization system 120, and in particular the light measuring instrument. In some embodiments, the same optical fiber or bundle of fibers 150 may be used to direct light to the tissue such that each fiber is coupled to each opening 154 to illuminate tissue outside the catheter 140 in one or more directions and to collect light from the tissue.

As shown in FIG. 4, the distal tip 148 of the catheter can include one or more flexible joints 160, 164, an electrode/first fiber ring 162 oriented to the first ring, and an electrode/second fiber ring 166 oriented to other rings. Each of the rings 162, 166 includes a port for an optical fiber. The rings 162, 166 can be spaced apart at a distance to accommodate the necessary spacing between the source fibers and the detector fibers. For example, one of a source fiber and a detector fiber are positioned at the opening in the ring 162 and the other of the source fiber and the detector fiber are positioned at the opening in the ring 166, and the distance between the rings 162, 166 is selected based on the type of tissue being investigated.

In some embodiments, the one or more openings 154 may be provided in any location on the walls of the distal tip 148. In some embodiments, the one or more openings 154 may be disposed circumferentially along the distal tip 148 around the entire circumference of the distal tip 148. In some embodiments, the one or more openings 154 may be disposed equidistantly from one another. The number of the openings may be determined by the desired angle of viewing coverage. For example, with 3 openings equally spaced, illumination and returned light occur at 120-degree increments (360 degrees divided by 3). In some embodiments, the one or more openings 154 may be provided in multiple rows along the walls of the distal tip 148. In some embodiments, the distal tip 148 may include 3 or 4 openings. In some embodiments, a single opening may be provided. In some embodiments, multiple openings 154 may be provided in the distal tip. In some embodiments, the distal tip 148 is provided with 3 side openings and 1 front opening. The one or more openings 154 may also serve as an irrigation port in connection with the irrigation system. In some embodiments light is only directed through some of the side openings 154. For example, in some embodiments there may exist 6 openings in the side wall 156, but light may be directed through only 3 of the openings, while the other openings may be used for irrigation.

FIG. 3 is a detailed view of the distal tip 148 of the catheter 140. The catheter 140 may include one or more pairs of light sources and detectors from the optical fibers 150. In some embodiments, each of such pairs comprises an optical fiber 151 to pass the light from the light source to the tissue to illuminate the tissue (also referred to as a sensor fiber) and an optical fiber 153 for collecting the light from the tissue and passing the collected light to the light measuring instrument (also referred to as a detector fiber). It should be noted that while FIG. 3 shows the source fiber distal of the detector fiber, the source fiber can also be placed proximal to the detector fiber. The separation 155 distance between the sensor fiber and the detector fiber varies depending on the depth of the tissue to be measured.

Unlike lesion progression analysis, which uses induced fluorescence to produce the desired optical response, wall measurement uses scattering as the optical means of detection. As photons emerge from the source, and as long as they are not absorbed, they will bump into the wall sub-structures and scatter throughout the tissue. Some photons will reach the detector after scattering and the time of travel between source and detector is measured. The time of travel is proportional to the wall thickness. And the resolution of the travel time increases with separation of source and detector.

Figure 10A:
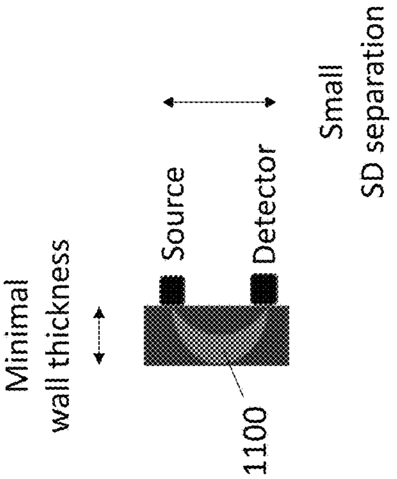
FIGS. 10A, 10B, and 10C are exemplary diagrams of wall-thickness measurement capabilities versus variations in optical source-detector separation.
Figure 10B:
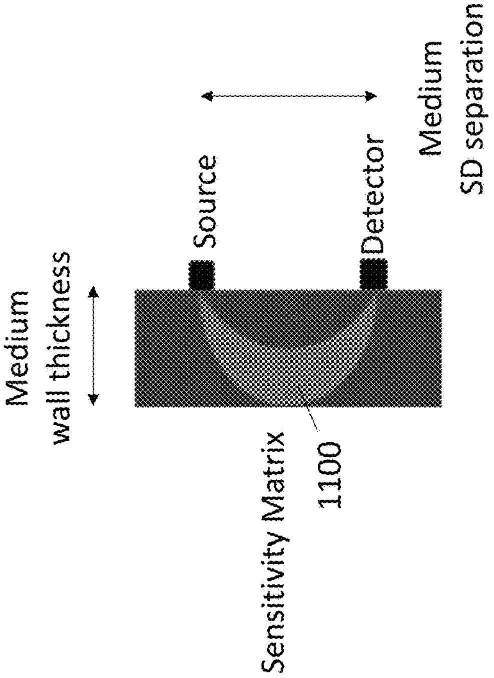
Figure 10C:
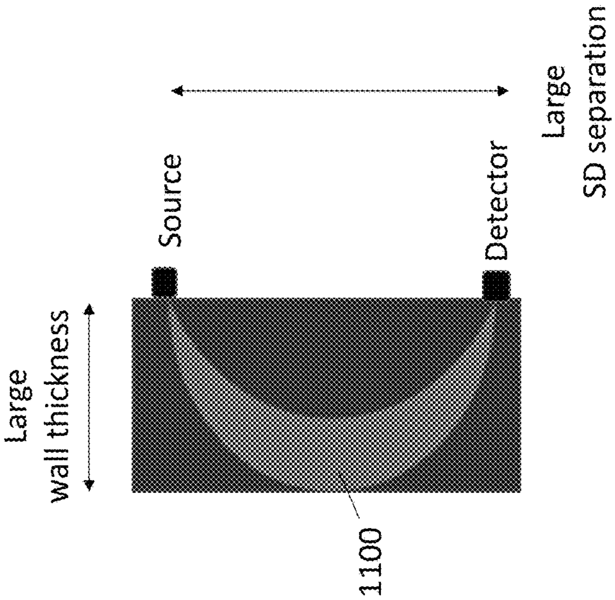

FIGS. 10A, 10B, and 10C are exemplary diagrams showing the sensitivity matrices 1100 in three scenarios of source-detector separation: short (FIG. 10A), medium (FIG. 10B), and long (FIG. 10C). The sensitivity matrices are 3-dimensional "banana" shapes showing the measurement range of corresponding to the depth of measurement and the SD separation distance with respect to various wall thicknesses.

The separation distance is accepted to be twice the depth to be measured with the desired precision (+/−0.5 mm). As such, various SD distances can accommodate different measurement ranges. For example, the SD short spacing can be between of 2 and 6 mm (for 1-3 mm atrial depth range), the SD medium spacing can be between 6 mm to about 12 mm (3 to 6 mm optimal for thicker atrial ranges), the SD long spacing can be between 12 mm to 20 mm (6 mm to 10 mm optimal for thick atrial wall thickness ranges).

In addition to the SD distance bounding the range of measurement, the distances are optimized to enhance the measurement resolution in a classic tradeoff between measurement range versus resolution. For cardiac wall measurement a desired resolution would be approximately 0.5 mm. This resolution provides a reasonable safety margin to ensure lesions are transmural (i.e., completely through the heart wall) but with enough resolution to prevent overheating of extra-cardiac structures like the esophagus.

In reference to FIG. 4, in some embodiments, it is desirable to have multiple sensor detector options since both need to be in contact with the myocardial surface in order to make the measurement. Multiple copies of sources and detectors increase the chance that at any time, at least two fibers are in contact with the heart in order to make the measurement.

In addition, multiple fibers allow the configuration of source and detector to vary so that different spacings can be made by any combination of two fibers. Narrower spacing can be used for thinner walls like in the atrium and wider-spaced pairs can be used for thicker walls like in the ventricles, while still using the same catheter.

To facilitate such measurements at different separation distances, in some embodiments, a series of spaced apart openings or ports 154 may be provided at the distal end of the catheter in a radial alignment with one another. The ports can be positioned at a variable distance from one another to provide different separation distances for the source fiber and detector fiber depending on the port placement of the source fiber and the detector fiber. For example, the separation distance between a source fiber placed in the most distal port and a detector fiber placed in the most proximal port is greater than the separation distance between a source and a detector fiber placed into the middle ports.

In some embodiments, the source fiber may be permanently placed into the most distal port and the placement of the detector fiber may be varied to achieve the desired separation distance. For example, in reference to FIG. 4, if a source fiber is placed into the most distal port 154, the separation distances of 2 mm, 6 mm and 13 mm can be achieved depending on the placement of the detector fiber. In some embodiments, the placement of either the source fiber or the detector fiber can be moved to achieve the desired separation distance.

In some embodiments, multiple series of such ports can be provided along the circumference of the distal tip. In some embodiments, the separation distances between the ports in each of the series may be the same. In some embodiments, the separation distances between the ports can be different for different series of ports to provide more selection of the separation distances.

In some embodiments, the fibers are maintained in radial alignment to enhance the chances that the fiber ports are in contact with the myocardial surface as contact is required to effectively detect NADH fluorescence but may not be required to detect wall thickness. This is because blood absorbs the illumination wavelength for NADH fluorescence. In some embodiments, the optical fibers are aligned along the long axis of the catheter (a straight line can be drawn thru the fiber sets and repeated radially around the catheter). This is important in some applications where the catheter is curved to reach targeted locations. Maintaining the alignment can increase the chances of fiber-tissue contact as the catheters bend in a planar fashion. In some embodiments, the fibers can be embedded in metal rings for simultaneous electrogram recording. The metal structure of the electrode can be manufactured to accept the fiber and more easily control the alignment of the fiber port to the bending of the catheter.

In some embodiments, the catheter may include a curve at the distal end. In such an embodiment, the fibers can be placed on the outside bend radius of the "J" shape of a curved catheter. The contact with the myocardial surface or other structure is more likely to occur on the outside radius of the "J" shape than on the inside radius. Having the fibers on the outside radius can reduce the number of fibers in the catheter as fibers on the inside radius of curvature would not make contact with the myocardial surface and are therefore not useful. Eliminating these inside-curve fiber ports will allow more fibers to the surface that is likely to be in contact with the myocardial surface.

Method of Use

Figure 5:
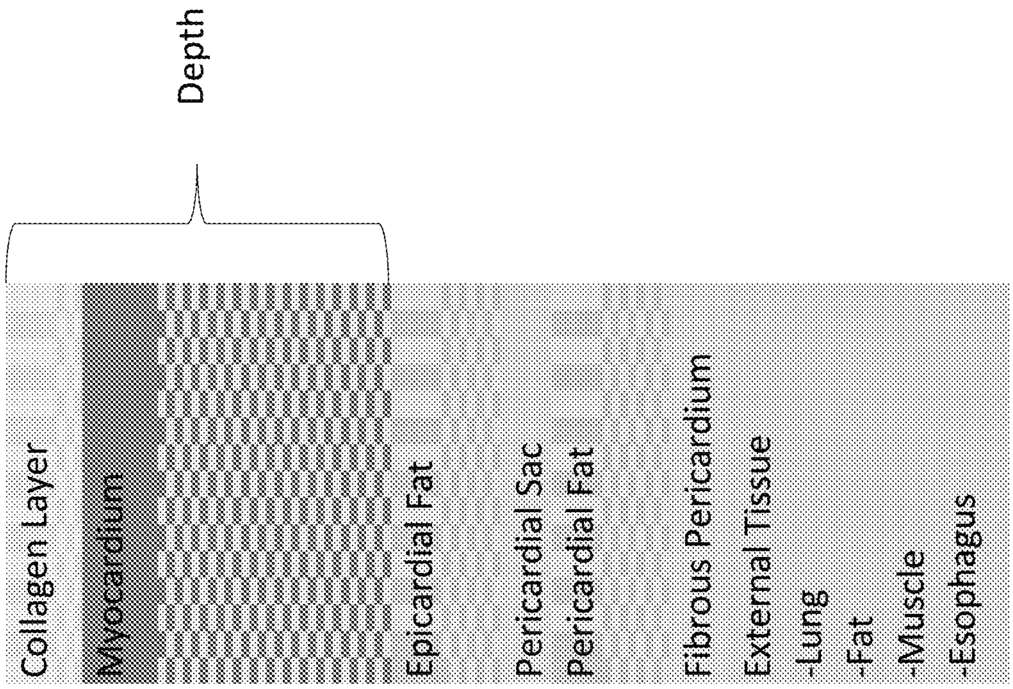
FIG. 5 illustrate an exemplary model of heart tissue.

In some embodiments, the depth or thickness of heart tissue can be measured using the systems and methods of the present disclosure. For example, FIG. 5 provides a model of the heart tissue and extra-cardiac layers expected to be encountered in arrhythmia procedures. In some embodiments, the heart wall thickness is defined as the distance from the 'top' surface (the inside of the heart) to the end of the myocardium, regardless of additional layers inside or outside of the heart.

In some embodiments, the wall thickness or depth of lesion can be determined by a time-resolved mathematical analysis of photon arrival time where photons are emitted from the source fibers and captured at the detector fibers. The measurement is enhanced by having multiple spaced SD pairs providing additional measurement range as described above. The concept in this approach requires short pulses of light from the source fibers and measuring the return time of the photons due to scattering within the various layers of FIG. 5. Each layer has different optical properties that affect the scattering time, and each layer border has a change of optical impedance that results in different return times of photons to the detector fiber. Multiple SD pairs can give redundant measurement information but with the limitations of range and specificity explained previously.

In a clinical example, if a physician wanted to measure cardiac wall thickness at a location that was unknown and likely to be in the range of capability of two SD pairs on the catheter, measurements can be taken with each pair independently and the results compared. This detection process and comparison can be automated by the optical instrument and displayed by the physician. The wall thickness measurement result can then be used to optimize the energy source to produce the desired lesion depth compared to wall thickness. A thinner wall will require less energy to form a lesion that is the thickness of the cardiac wall and does not damage layers beyond the myocardium (see FIG. 5).

More specifically, short picosecond pulses of light over the specific wavelength range (700 nm to 1200 nm from a wide-band illumination source are sent into the tissue structure. The pulses must be this short in duration to end before the nearest photons reach the nearest detector or the emitting light will mask the response. The return time can be measured, and this time is correlated to the boundaries between layers and hence the distance between boundaries. If the layers are known (see below) then the time responses can be added to determine the layer thicknesses and the overall thickness of the layers desired to be analyzed. For example, if 3 layers are known, the third signal to return to the detector is the layer of interest and the time delay in the return of the third signal can be correlated to the depth of that particular layer. If the number of layers are unknown, as can be the case with fibrous or collagen in the aging heart, the confidence in the measurement decreases. However, this can be factored into an algorithm to still determine wall thickness but with less resolution, as is described below.

For situations where the specific layers are known or unknown, the data from the detectors can be analyzed using Partial-Least-Squares Regression (PLS) or Multi-layer fitting to determine layer thickness. PLS is a statistical method that finds a linear regression model by projecting the predicted variables and the observed variables into a new data set. The linear regression is then performed on the new data set as opposed to the original data in an attempt to find a solution that makes, in relevant applications, clinical sense. The PLS can map the data in higher-dimensional space against a dependent variable (myocardial depth), then different combinations of distance and time-of-flight can be used to 'collapse' the higher dimensions and linearize the data against depth. The multi-layer fitting attempts to optimize to determine what combination of layer thicknesses and optical properties 'make most sense' based on observed data from several time-resolved detectors. The fitting algorithm takes advantage of known biological ranges of structure thicknesses. As examples, most the atrial wall is between 2 mm and 6 mm thick, the collagen layer on the atrial endocardial surface ranges from 0 mm to approximately 1.5 mm, and the pericardial sac is approximately 0.5 to 1 mm thick. These known ranges are taken into account to determine a calculation of how deep a lesion needs to be to be confident that the lesion is transmural but not damaging the structures outside of the heart. To take this example set further, if there are three photon return time signals that correlate to a collagen layer, myocardial layer and pericardial sac layer, we would expect that cumulative thickness to be less than the maximum expected sum of 1.5 mm (collagen) plus 6 mm (myocardium) plus 1 mm (pericardium) equaling 8.5 mm. A calculation with this result would indicate a collagen layer and a distance to the esophagus of about 8.5 mm or less with a resolution of approximately +0/−4 mm dominated by the range of myocardium variability. If the system was able to detect and apply a priori knowledge to the situation, the resolution can be improved.

In some embodiments, a-priori knowledge of the tissue can be applied to make the wall thickness or lesion depth measurement more precise. Since the system of this embodiment has the capability to detect NADH and collagen fluorescence, that measurement can be taken prior to the wall thickness measurement to determine if there is a layer of collagen on the myocardial surface. The collagen may or may not be a previous lesion but it's presence or lack of provides information. To do so, the normal illumination to induce NADH fluorescence is emitted and the response is analyzed. If collagen is detected, the presence of this layer can be fed into the PLS Multi-layer fitting algorithm where it will know that the first response to the short pulse light is due to scattering within the collagen layer (because it is the first layer) and that the second response is the myocardial layer. On the contrary, if the illumination response only shows NADH fluorescence then the first returned photons correspond to myocardium and its wall thickness. With no collagen layer, the uncertainty in the wall measurement is reduced to the accuracy of each layer measurement (0.5 mm desired) and the thickness range of the pericardial sac (1.5 mm).

Figure 6:
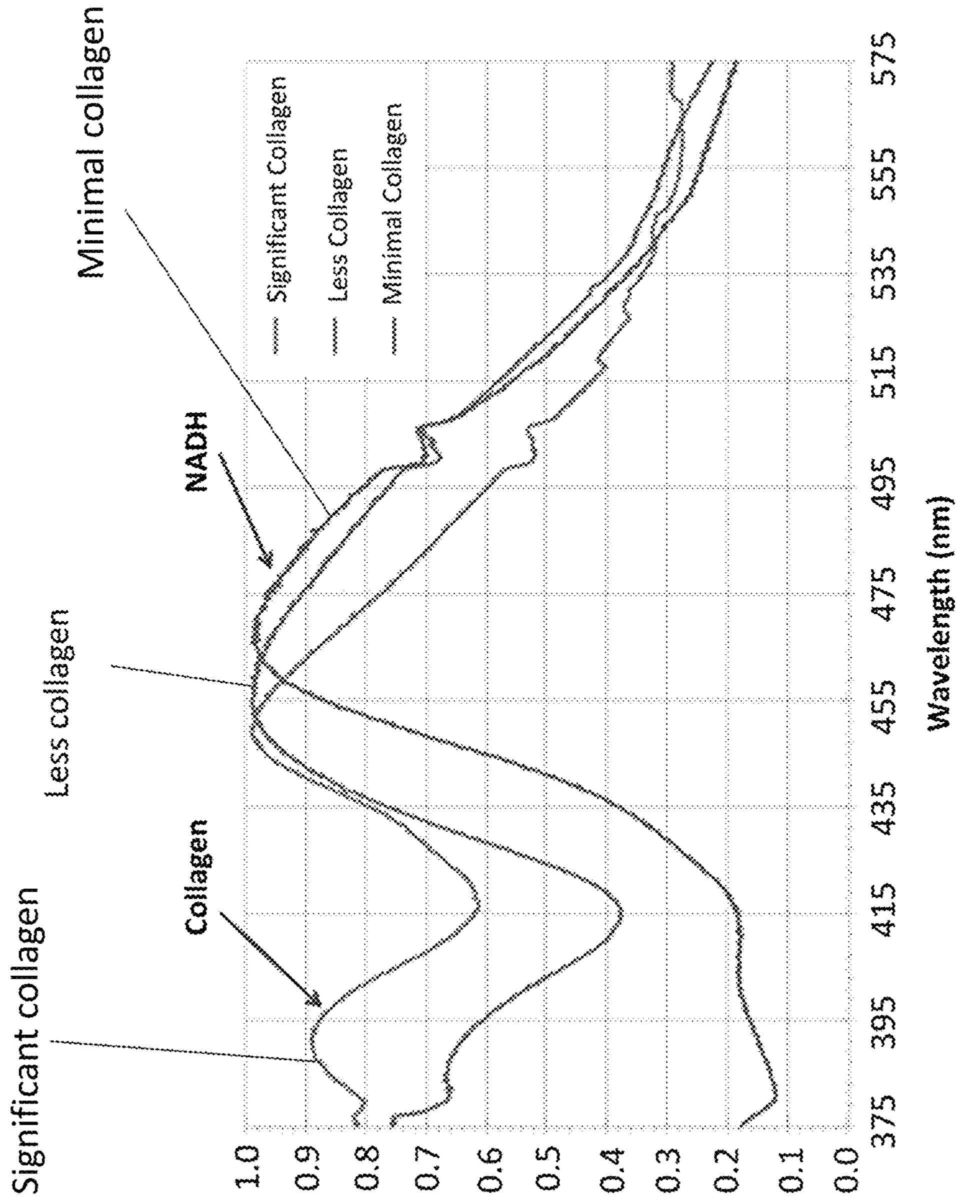
FIGS. 6 and 7 illustrate exemplary graphs suitable for determining tissue composition and tracking lesion formation.

In reference to FIG. 6, in some embodiments, the systems and methods of the present disclosure can be used to determine tissue composition. For example, in some embodiments, the spectral signature may be collected over a range of wavelength that encompasses collagen fluorescence. The spectral pattern of collagenous tissue is different than the one seen on healthy myocardium. When illuminated in this case with a 355 nm UV light source, the peak of the spectrum shifts to the left (from about 470 nm to about 445 nm) when imaging over collagenous tissue to shorter wavelengths due to increased effect of collagen fluorescence. This may be used by the user to identify the area that is being treated as being mostly myocardium or being covered by collagen, which is harder to ablate.

Figure 7:
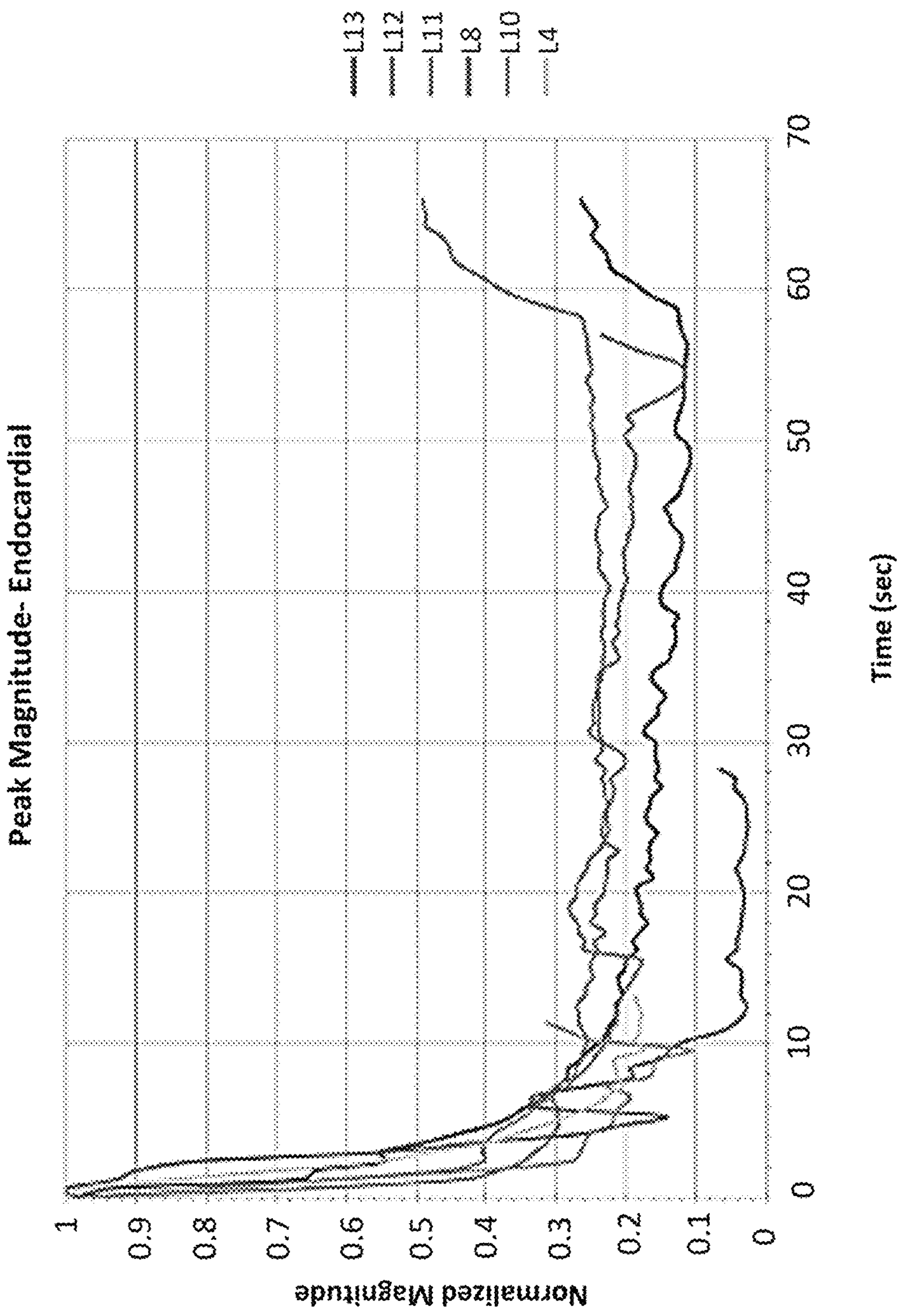

In some embodiments, the instant systems can also be used to track lesion formation during ablation. In some embodiments, the digital image that is produced by analyzing the light data may be used to do the 2D and 3D reconstruction of the lesion, showing size, shape and any other characteristics necessary for analysis. In some embodiments, the fiber set or image bundle may be connected to the spectrometer 124, which may generate a digital image of the lesion being examined from NADH fluorescence (fNADH), which can be displayed on the display 180. In some embodiment, these images can be displayed to the user in real time. In some embodiments, the images can be a graph showing a change in the NADH fluorescence coming from the tissue. The images can be analyzed by using software to obtain real-time details (e.g., intensity or radiated energy in a specific site of the image) to help the user to determine whether further intervention is necessary or desirable. In some embodiments, the NADH fluorescence may be conveyed directly to the computer system 126. FIG. 7 presents an exemplary graph that can be presented to the user to track lesion formation. As is shown in FIG. 7, the NADH fluorescence decreases as the tissue is being ablated and the ablation can be completed based on a desired reduction in the NADH fluorescence.

Figure 8:
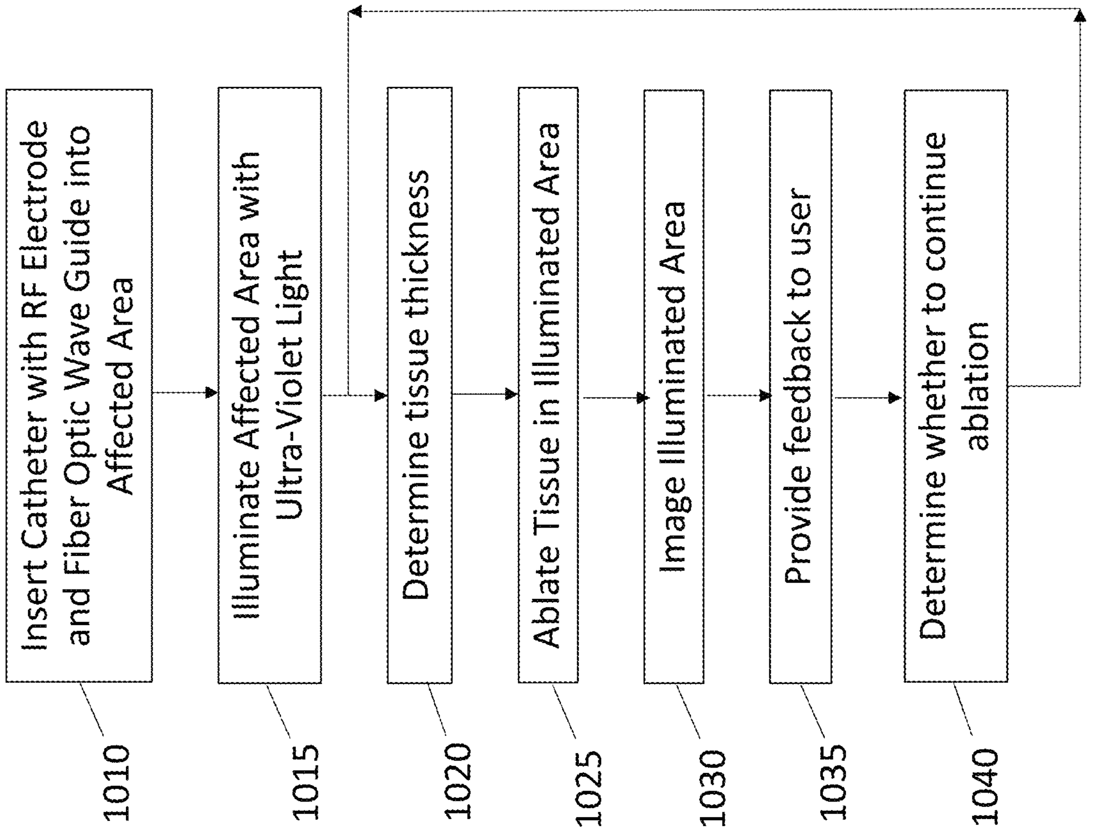
FIG. 8 is an exemplary flow chart of a method of using a system of the present disclosure.

In reference to FIG. 8, operation of the systems 100 of the present disclosure is illustrated. Initially, the catheter 140 is inserted into the area of heart tissue affected by the atrial fibrillation, such as the pulmonary vein/left atrial junction or another area of the heart (step 1010). Blood may be removed from the visual field, for example, by irrigation or direct myocardial contact. The affected area may be illuminated by light energy from the light source (step 1015).

The light reflected from the tissue may be collected and the tissue thickness can be determined (step 1020) as described above. Tissue in the illuminated area may be ablated (step 1025), either before, after, or during illumination. Either point-to-point RF ablation or cryoablation or laser or other known ablation procedures may be employed using the systems of the present disclosure. In some embodiments, the tissue thickness determined by the system can be to adjust the ablation of the tissue. For example, the system can adjust various ablation parameters, including but not limited to ablation energy type, the timing and/or duration of the application of the ablation energy, and/or ablation energy level. The illuminated area may be imaged again for the NADH fluorescence (step 1030), and the data may be used to provide feedback to the user on the progression of the lesion formation (step 1035) to help the user to determine when to stop ablation (step 1040). For example, if the NADH fluorescence has been sufficiently reduced, the user can stop ablating the tissue, but if the NADH fluorescence is still higher than a pre-selected level, the ablation can continue.

FIG. 8 illustrates the steps being performed sequentially, many of the steps may be performed simultaneously or nearly simultaneously, or in a different order than shown in FIG. 8. For example, the ablation, imaging and display can occur at the same time, and the identification of the ablated and unablated tissue can occur while ablating the tissue.

The system performs at its best for the physician when the combination of wall thickness and lesion depth are used at a given location. Having wall thickness without lesion depth or having lesion depth without wall thickness each leave the physician unsure that a transmural lesion has been made. If the lesion depth is less than transmural, unwanted electrical propagation of arrhythmias can occur in the un-ablated tissue. If the lesion depth exceeds the wall thickness, damage to structures such as the esophagus can and do occur. As such, the combination of knowing the lesion depth and the target wall thickness can determine transmurality of the lesion and once that is achieved there is no reason to keep applying energy and the extra-cardiac structures can be spared thermal damage.

The foregoing disclosure has been set forth merely to illustrate various non-limiting embodiments of the present disclosure and is not intended to be limiting. Since modifications of the disclosed embodiments incorporating the spirit and substance of the disclosure may occur to persons skilled in the art, the presently disclosed embodiments should be construed to include everything within the scope of the appended claims and equivalents thereof.

What is claimed is:

1. A catheter system for determining tissue thickness, comprising:

a catheter comprising a catheter body and a distal tip positioned at a distal end of the catheter body;

the distal tip comprising a tip and a plurality of electrode rings disposed proximally to the tip, the plurality of electrode rings being spaced apart from one another in a longitudinal direction and the plurality of electrode rings being configured to function as an electrode, the tip comprising at least one opening, each of the plurality of electrode rings comprising at least one opening, wherein the at least one opening of the tip and the at least one opening of each of the plurality of electrode rings define one or more source openings and one or more detector openings, the one or more source openings and the one or more detector openings being aligned in a longitudinal arrangement along a length of the distal tip and being paired and spaced apart from one another, the one or more source openings in the distal tip being configured for passing light energy to a tissue, and the one or more detector openings in the distal tip being configured for passing light energy from the tissue; and a visualization system comprising a light source, a light measuring instrument, and one or more optical fibers in communication with the light source and the light measuring instrument and extending through the catheter body to the distal tip, the one or more optical fibers comprising one or more source fibers to pass light energy to the tissue through the one or more source openings and one or more detector fibers to detect light energy from the tissue through one of the one or more detector openings, wherein a distal end of at least one of the one or more source fibers is permanently placed into a source opening of a most distal electrode ring and a distal end of the one or more detector fibers is configured to be variably positioned at the one or more detector openings of any one of the plurality of electrode rings to achieve a desired separation distance between the respective distal ends based on a thickness of the tissue to be measured.

2. The catheter system of claim 1, wherein the light energy for illuminating the tissue has at least one wavelength between about 750 nm and about 1400 nm.

3. The catheter system of claim 1, wherein the separation distance between one of the one or more source openings and one of the one or more detector openings is proportional to the thickness of the tissue.

4. The catheter system of claim 1, wherein the separation distance between one of the one or more source openings and one of the one or more detector openings is in a range of 1 to 15 mm.

5. The catheter system of claim 1, further comprising a processor in communication with the light measuring instrument, the processor being programmed to determine a thickness of the tissue using information from the one or more detector fibers and the separation distance between the one or more source fibers and the one or more detector fibers.

6. The catheter system of claim 1, wherein the one or more source openings and the one or more detector openings are disposed circumferentially along the distal tip.

7. The catheter system of claim 1, wherein the one or more detector openings include multiple detector openings that are each aligned with and positioned at different distances from a corresponding source opening of the one or more source openings.

8. The catheter system of claim 1, further comprising an ablation element configured to deliver ablation energy to the tissue, wherein the ablation energy is selected from a group consisting of pulsed field ablation energy, electroporation energy, radiofrequency (RF) energy, microwave energy, electrical energy, electromagnetic energy, cryoenergy, laser energy, ultrasound energy, acoustic energy, chemical energy, thermal energy and combinations thereof.

9. The catheter system of claim 1, wherein the tissue comprises ablated tissue.

10. A catheter system for determining tissue thickness, comprising:

a catheter comprising a catheter body and a distal tip positioned at a distal end of the catheter body, the distal tip comprising a tip and a plurality of electrode rings disposed proximally to the tip, the plurality of electrode rings being spaced apart from one another in a longitudinal direction and the plurality of electrode rings being configured to function as an electrode, the tip comprising at least one opening, and each of the plurality of electrode rings comprising at least one opening, wherein the at least one opening of the tip and the at least one opening of each of the plurality of electrode rings define one or more source openings and one or more detector openings, the one or more source openings in the distal tip being configured for passing light energy to a tissue, the one or more detector openings in the distal tip configured for passing light energy from the tissue, the one or more source openings and the one or more detector openings being aligned in a longitudinal arrangement along a length of the distal tip and being paired and spaced apart from one another, one or more source fibers having a distal tip disposed at one or more source openings and being configured to pass light energy to the tissue through the one or more source openings, and one or more detector fibers having a distal tip disposed at one of the one or more detector openings and being configured to detect light energy from the tissue through the one of the one or more detector openings, wherein respective rings of the plurality of electrode rings are spaced apart from one another, and wherein a distal end of at least one of the one or more source fibers is permanently placed into a source opening of a most distal electrode ring and a distal end of the one or more detector fibers is configured to be variably positioned at the one or more detector openings of any one of the plurality of electrode rings to achieve a desired separation distance between the respective distal ends based on a thickness of the tissue to be measured.

11. The catheter system of claim 10, further comprising an ablation element configured to deliver ablation energy to the tissue, wherein the ablation energy is selected from a group consisting of pulsed field ablation energy, electroporation energy, radiofrequency (RF) energy, microwave energy, electrical energy, electromagnetic energy, cryoenergy, laser energy, ultrasound energy, acoustic energy, chemical energy, thermal energy and combinations thereof.

12. The catheter system of claim 10, wherein the tissue comprises ablated tissue.

13. A system for determining tissue thickness, comprising:

a catheter comprising a catheter body and a distal tip positioned at a distal end of the catheter body;

the distal tip comprising a tip and a plurality of electrode rings disposed proximally to the tip, the plurality of electrode rings being spaced apart from one another in a longitudinal direction and the plurality of electrode rings being configured to function as an electrode, the tip comprising at least one opening, each of the plurality of electrode rings comprising at least one opening, wherein the at least one opening of the tip and the at least one opening of each of the plurality of electrode rings define one or more source openings and one or more detector openings, the one or more source openings and the one or more detector openings being aligned in a longitudinal arrangement along a length of the distal tip and being paired and spaced apart from one another, the one or more source openings in the distal tip being configured for passing light energy to a tissue;

the one or more detector openings in the distal tip being configured for passing light energy from the tissue;

a visualization system comprising a light source, a light measuring instrument, and one or more optical fibers in communication with the light source and the light measuring instrument and extending through the catheter body to the distal tip, the one or more optical fibers comprising one or more source fibers to pass light energy to the tissue through one of the one or more source openings and one or more detector fibers to detect light energy from the tissue through one of the one or more detector openings; and a processor in communication with the light measuring instrument, the processor being programmed to determine a thickness of the tissue using information from the one or more detector fibers, wherein the thickness of the tissue is used to determine one or more ablation parameters, wherein a distal end of at least one of the one or more source fibers is permanently placed into a source opening of a most distal electrode ring and a distal end of the one or more detector fibers is configured to be variably positioned at the one or more detector openings of any one of the plurality of electrode rings to achieve a desired separation distance between the respective distal ends based on a thickness of the tissue to be measured.

14. The system of claim 13, wherein the light energy for illuminating the tissue has at least one wavelength between about 750 nm and about 1400 nm.

15. The system of claim 13, wherein the separation distance between one of the one or more source openings and one of the one or more detector openings is proportional to the thickness of the tissue.

16. The system of claim 13, wherein the separation distance between one of the one or more source openings and one of the one or more detector openings is in a range of 1 to 15 mm.

17. The system of claim 13, wherein the one or more source openings and the one or more detector openings are disposed circumferentially along the distal tip.

18. The system of claim 13, wherein the one or more detector openings include multiple detector openings that are each aligned with and positioned at different distances from the one or more source openings.

19. The system of claim 13, further comprising an ablation element configured to deliver ablation energy to the tissue, wherein the ablation energy is selected from a group consisting of pulsed field ablation energy, electroporation energy, radiofrequency (RF) energy, microwave energy, electrical energy, electromagnetic energy, cryoenergy, laser energy, ultrasound energy, acoustic energy, chemical energy, thermal energy and combinations thereof.

20. The system of claim 13, wherein the tissue comprises ablated tissue.

21. A method for determining tissue thickness, comprising:

advancing a catheter to a tissue, the catheter comprising a catheter body; a distal tip positioned at a distal end of the catheter body, the distal tip comprising a tip and a plurality of electrode rings disposed proximally to the tip, the plurality of electrode rings being spaced apart from one another in a longitudinal direction and the plurality of electrode rings being configured to function as an electrode, the tip comprising at least one opening, each of the plurality of electrode rings comprising at least one opening, the at least one opening of the tip and the at least one opening of each of the plurality of electrode rings define one or more source openings and one or more detector openings, the one or more source openings and the one or more detector openings being aligned in a longitudinal arrangement along a length of the distal tip and being paired and spaced apart from one another, the one or more source openings configured for passing light energy to a tissue and the one or more detector openings configured for passing light energy from the tissue; and one or more optical fibers extending through the catheter body and comprising one or more source fibers to pass light energy to the tissue through the one or more source openings and one or more detector fibers to detect light energy from the tissue through one of the one or more detector openings, a distal end of at least one of the one or more source fibers is permanently placed into a source opening of a most distal electrode ring and a distal end of the one or more detector fibers is configured to be variably positioned at the one or more detector openings of any one of the plurality of electrode rings to achieve a desired separation distance between the respective distal ends based on a thickness of the tissue to be measured;

illuminating the tissue through the one or more source openings in the distal tip of the catheter using the one or more source fibers;

collecting light reflected from the tissue through the one or more detector openings from the one or more detector fibers and directing the collected light to a light measuring instrument;

determining a thickness of the tissue using the collected light from the one or more detector openings; and determining one or more ablation parameters using the thickness of the tissue.

22. The method of claim 21, wherein the light energy for illuminating the tissue has at least one wavelength between about 750 nm and about 1400 nm.

23. The method of claim 21, wherein the separation distance between one of the one or more source openings and one of the one or more detector openings is proportional to the thickness of the tissue.

24. The method of claim 21, wherein the separation distance between one of the one or more source openings and one of the one or more detector openings is in a range of 1 to 15 mm.

25. The method of claim 21, further comprising delivering ablation energy to the tissue, wherein the ablation energy is selected from a group consisting of pulsed field ablation energy, electroporation energy, radiofrequency (RF) energy, microwave energy, electrical energy, electromagnetic energy, cryoenergy, laser energy, ultrasound energy, acoustic energy, chemical energy, thermal energy and combinations thereof.

26. The method of claim 21, wherein the tissue comprises ablated tissue.

* * * * *